US011693259B2

(12) United States Patent
Buscemi et al.

(10) Patent No.: US 11,693,259 B2
(45) Date of Patent: *Jul. 4, 2023

(54) METHODS FOR THE TREATMENT OF REFRACTIVE ERROR USING ACTIVE STIMULATION

(71) Applicant: ACUCELA INC., Seattle, WA (US)

(72) Inventors: Philip M. Buscemi, Mount Pleasant, SC (US); Ryo Kubota, Seattle, WA (US)

(73) Assignee: ACUCELA INC., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/820,738

(22) Filed: Aug. 18, 2022

(65) Prior Publication Data

US 2022/0404638 A1    Dec. 22, 2022

Related U.S. Application Data

(63) Continuation of application No. 17/650,266, filed on Feb. 8, 2022, now Pat. No. 11,467,423, which is a
(Continued)

(51) Int. Cl.
G02C 7/04 (2006.01)
G02B 27/01 (2006.01)
G02C 7/14 (2006.01)

(52) U.S. Cl.
CPC .............. *G02C 7/04* (2013.01); *G02B 27/017* (2013.01); *G02C 7/14* (2013.01); *G02B 2027/0178* (2013.01); *G02C 2202/24* (2013.01)

(58) Field of Classification Search
CPC .......... G02B 27/017; G02B 2027/0178; G02C 2202/24; G02C 7/00; G02C 7/04; G02C 7/14
(Continued)

(56) References Cited

U.S. PATENT DOCUMENTS 6,516,808 B2   2/2003   Schulman
7,018,040 B2   3/2006   Blum
(Continued)

FOREIGN PATENT DOCUMENTS

EP   3153139   4/2017
EP   3413116   12/2018
(Continued)

OTHER PUBLICATIONS

Adler, Daniel, et al., "The possible effect of under correction on myopic progression in children," Clin Exp Optom., 89:315-321 (2006).
(Continued)

*Primary Examiner* — William R Alexander
(74) *Attorney, Agent, or Firm* — Fisherbroyles LLP; John Shimmick

(57) ABSTRACT

Systems, devices, apparatuses and methods for an active projection system that may be incorporated into spectacles, contact lenses or provided as an add-on layer to existing spectacles or lenses. The active projection system operates to generate a stimulus or stimuli for viewing by a person's eye. The stimulus or stimuli creates an image that is defocused in front of the person's retina and can assist in slowing or stopping the progression of myopia or other refractive errors in the person.

19 Claims, 27 Drawing Sheets

Related U.S. Application Data continuation of application No. 17/303,889, filed on Jun. 9, 2021, now Pat. No. 11,281,022.

(60) Provisional application No. 63/037,504, filed on Jun. 10, 2020.

(58) Field of Classification Search
USPC ..................................................... 351/159.6
See application file for complete search history.

(56) References Cited

U.S. PATENT DOCUMENTS

| | | |
|---|---|---|
| 8,246,167 B2 | 8/2012 | Legerton |
| 8,432,124 B2 | 4/2013 | Foster |
| 8,662,664 B2 | 3/2014 | Artal Soriano |
| 8,857,983 B2 | 10/2014 | Pugh |
| 9,345,813 B2 | 5/2016 | Hogg |
| 9,482,882 B1 | 11/2016 | Hanover |
| 9,482,883 B1 | 11/2016 | Meisenholder |
| 9,726,904 B1 | 8/2017 | Lin |
| 9,763,827 B2 | 9/2017 | Kelleher |
| 9,885,884 B2 | 2/2018 | Drobe |
| 9,918,894 B2 | 3/2018 | Lam |
| 9,962,071 B2 | 5/2018 | Yates |
| RE47,006 E | 8/2018 | To |
| 10,133,092 B2 | 11/2018 | Tsubota |
| 10,139,521 B2 | 11/2018 | Tran |
| 10,146,067 B2 | 12/2018 | Tsai |
| 10,231,897 B2 | 3/2019 | Tse |
| 10,268,050 B2 | 4/2019 | To |
| 10,288,909 B1 | 5/2019 | Youssef |
| 10,591,745 B1 | 3/2020 | Lin |
| 10,788,686 B2 | 9/2020 | Tsai |
| 10,884,264 B2 | 1/2021 | Hones |
| 10,921,612 B2 | 2/2021 | Zhou |
| 10,993,515 B1 | 5/2021 | Kim |
| 11,000,186 B2 | 5/2021 | Linder |
| 11,163,166 B1 | 11/2021 | Ebert |
| 11,187,921 B2 | 11/2021 | Zhou |
| 11,219,287 B1 | 1/2022 | Kim |
| 11,275,259 B2 | 3/2022 | Kubota |
| 11,281,022 B2 | 3/2022 | Buscemi |
| 11,320,674 B2 | 5/2022 | Kubota |
| 11,358,001 B2 | 6/2022 | Kubota |
| 11,366,339 B2 | 6/2022 | Kubota |
| 11,366,341 B1 | 6/2022 | Kubota |
| 11,402,662 B2 | 8/2022 | Wyss |
| 11,409,136 B1 | 8/2022 | Kubota |
| 11,415,818 B2 | 8/2022 | Olgun |
| 11,444,488 B2 | 9/2022 | Bohn |
| 11,446,514 B2 | 9/2022 | Bahmani |
| 11,460,720 B1 | 10/2022 | Kubota |
| 11,467,423 B2 | 10/2022 | Buscemi |
| 11,467,426 B2 | 10/2022 | Kubota |
| 11,467,428 B2 | 10/2022 | Kubota |
| 11,480,813 B2 | 10/2022 | Kubota |
| 11,531,216 B2 | 12/2022 | Kubota |
| 2002/0186345 A1 | 12/2002 | Duppstadt |
| 2003/0011745 A1 | 1/2003 | Molebny |
| 2004/0237971 A1 | 12/2004 | Radhakrishnan |
| 2004/0246441 A1 | 12/2004 | Stark |
| 2004/0257529 A1 | 12/2004 | Thomas |
| 2005/0258053 A1 | 11/2005 | Sieg |
| 2006/0082729 A1 | 4/2006 | To |
| 2007/0002452 A1 | 1/2007 | Munro |
| 2007/0076217 A1 | 4/2007 | Baker |
| 2007/0115431 A1 | 5/2007 | Smith, III |
| 2007/0127349 A1 | 6/2007 | Hotta |
| 2007/0281752 A1 | 12/2007 | Lewis |
| 2008/0291391 A1 | 11/2008 | Meyers |
| 2008/0309882 A1 | 12/2008 | Thorn |
| 2009/0002631 A1 | 1/2009 | Campbell |
| 2009/0187242 A1 | 7/2009 | Weeber |
| 2009/0201460 A1 | 8/2009 | Blum |
| 2009/0204207 A1 | 8/2009 | Blum |
| 2010/0076417 A1 | 3/2010 | Suckewer |
| 2010/0294675 A1 | 11/2010 | Mangano |
| 2010/0296058 A1 | 11/2010 | Ho |
| 2011/0085129 A1 | 4/2011 | Legerton |
| 2011/0153012 A1 | 6/2011 | Legerton |
| 2011/0157554 A1 | 6/2011 | Kawai |
| 2011/0202114 A1 | 8/2011 | Kessel |
| 2012/0055817 A1 | 3/2012 | Newman |
| 2012/0062836 A1 | 3/2012 | Tse |
| 2012/0199995 A1 | 8/2012 | Pugh |
| 2012/0206485 A1 | 8/2012 | Osterhout |
| 2012/0212399 A1 | 8/2012 | Border |
| 2012/0215291 A1 | 8/2012 | Pugh |
| 2013/0027655 A1 | 1/2013 | Blum |
| 2013/0072828 A1 | 3/2013 | Sweis |
| 2013/0194540 A1 | 8/2013 | Pugh |
| 2013/0278887 A1 | 10/2013 | Legerton |
| 2013/0317487 A1 | 11/2013 | Luttrull |
| 2014/0039048 A1 | 2/2014 | Bavik |
| 2014/0039361 A1 | 2/2014 | Yin |
| 2014/0194773 A1 | 7/2014 | Pletcher |
| 2014/0218647 A1 | 8/2014 | Blum |
| 2014/0240665 A1 | 8/2014 | Pugh |
| 2014/0268029 A1 | 9/2014 | Pugh |
| 2014/0277291 A1 | 9/2014 | Pugh |
| 2014/0379054 A1 | 12/2014 | Cooper |
| 2015/0057701 A1 | 2/2015 | Kelleher |
| 2015/0109574 A1 | 4/2015 | Tse |
| 2015/0160477 A1 | 6/2015 | Dai |
| 2015/0200554 A1 | 7/2015 | Marks |
| 2015/0241706 A1 | 8/2015 | Schowengerdt |
| 2016/0016004 A1 | 1/2016 | Hudson |
| 2016/0056498 A1 | 2/2016 | Flitsch |
| 2016/0067037 A1 | 3/2016 | Rosen |
| 2016/0067087 A1 | 3/2016 | Tedford |
| 2016/0091737 A1 | 3/2016 | Kim |
| 2016/0143801 A1 | 5/2016 | Lam |
| 2016/0158486 A1 | 6/2016 | Colbaugh |
| 2016/0212404 A1 | 7/2016 | Maiello |
| 2016/0270656 A1 | 9/2016 | Samec |
| 2016/0377884 A1 | 12/2016 | Lau |
| 2017/0000326 A1 | 1/2017 | Samec |
| 2017/0001032 A1 | 1/2017 | Samec |
| 2017/0010480 A1 | 1/2017 | Blum |
| 2017/0014074 A1 | 1/2017 | Etzkorn |
| 2017/0055823 A1 | 3/2017 | Lu |
| 2017/0072218 A1 | 3/2017 | Rucker |
| 2017/0078623 A1 | 3/2017 | Hilkes |
| 2017/0097519 A1 | 4/2017 | Lee |
| 2017/0115512 A1 | 4/2017 | Pugh |
| 2017/0184875 A1 | 6/2017 | Newman |
| 2017/0229730 A1 | 8/2017 | Flitsch |
| 2017/0236255 A1 | 8/2017 | Wetzstein |
| 2017/0270636 A1 | 9/2017 | Shtukater |
| 2017/0276963 A1 | 9/2017 | Brennan |
| 2017/0307779 A1 | 10/2017 | Marullo |
| 2018/0017810 A1 | 1/2018 | Wu |
| 2018/0017814 A1 | 1/2018 | Tuan |
| 2018/0052319 A1 | 2/2018 | Mccabe |
| 2018/0055351 A1 | 3/2018 | Yates |
| 2018/0074322 A1 | 3/2018 | Rousseau |
| 2018/0090958 A1 | 3/2018 | Steger |
| 2018/0092738 A1 | 4/2018 | Tai |
| 2018/0136486 A1 | 5/2018 | Macnamara |
| 2018/0136491 A1 | 5/2018 | Ashwood |
| 2018/0161231 A1 | 6/2018 | Tse |
| 2018/0173010 A1 | 6/2018 | Harant |
| 2018/0188556 A1 | 7/2018 | Portney |
| 2018/0221140 A1 | 8/2018 | Rosen |
| 2018/0264284 A1 | 9/2018 | Alvarez |
| 2018/0275427 A1 | 9/2018 | Lau |
| 2018/0345034 A1 | 12/2018 | Butzloff |
| 2019/0033618 A1 | 1/2019 | Choi |
| 2019/0033619 A1 | 1/2019 | Neitz |
| 2019/0038123 A1 | 2/2019 | Linder |
| 2019/0049730 A1 | 2/2019 | Miller |
| 2019/0076241 A1 | 3/2019 | Alarcon Heredia |
| 2019/0092545 A1 | 3/2019 | Oag |
| 2019/0107734 A1 | 4/2019 | Lee |

(56) References Cited

U.S. PATENT DOCUMENTS

| | | |
|---|---|---|
| 2019/0113757 A1 | 4/2019 | Van Heugten |
| 2019/0129204 A1 | 5/2019 | Tsubota |
| 2019/0227342 A1 | 7/2019 | Brennan |
| 2019/0235279 A1 | 8/2019 | Hones |
| 2019/0247675 A1 | 8/2019 | Legerton |
| 2019/0250432 A1 | 8/2019 | Kim |
| 2019/0314147 A1 | 10/2019 | Blum |
| 2020/0033637 A1 | 1/2020 | Jamshidi |
| 2020/0073148 A1 | 3/2020 | Alhaideri |
| 2020/0089023 A1 | 3/2020 | Zhou |
| 2020/0108272 A1 | 4/2020 | Bahmani |
| 2020/0110265 A1 | 4/2020 | Serdarevic |
| 2020/0133024 A1 | 4/2020 | Paune Fabre |
| 2020/0142219 A1 | 5/2020 | Rousseau |
| 2020/0183169 A1 | 6/2020 | Peng |
| 2020/0264455 A1 | 8/2020 | Olgun |
| 2020/0360184 A1 | 11/2020 | Xiao |
| 2021/0018762 A1 | 1/2021 | Zheleznyak |
| 2021/0031051 A1 | 2/2021 | Kubota |
| 2021/0048690 A1 | 2/2021 | Guillot |
| 2021/0069524 A1 | 3/2021 | Kubota |
| 2021/0231977 A1 | 7/2021 | Zhou |
| 2021/0263336 A1 | 8/2021 | Gupta |
| 2021/0298440 A1 | 9/2021 | Kim |
| 2021/0329764 A1 | 10/2021 | Linder |
| 2021/0356767 A1 | 11/2021 | Kubota |
| 2021/0376661 A1 | 12/2021 | Bohn |
| 2021/0379399 A1 | 12/2021 | Buscemi |
| 2021/0382325 A1 | 12/2021 | Kubota |
| 2021/0382326 A1 | 12/2021 | Kubota |
| 2021/0389607 A1 | 12/2021 | Buscemi |
| 2022/0107508 A1 | 4/2022 | Zhou |
| 2022/0179213 A1 | 6/2022 | Zhou |
| 2022/0231523 A1 | 7/2022 | Bristol |
| 2022/0397775 A1 | 12/2022 | Bahmani |

FOREIGN PATENT DOCUMENTS

| | | |
|---|---|---|
| KR | 20180038359 A | 4/2018 |
| TW | M356929 | 5/2009 |
| TW | 201234072 | 8/2012 |
| TW | 201734580 | 10/2017 |
| WO | 2009074638 A3 | 6/2009 |
| WO | 2009121810 | 10/2009 |
| WO | 2010015255 A1 | 2/2010 |
| WO | 2010043599 | 4/2010 |
| WO | 2011089042 | 7/2011 |
| WO | 2012136470 | 10/2012 |
| WO | 2013087518 | 6/2013 |
| WO | 2013158418 | 10/2013 |
| WO | 2014033035 | 3/2014 |
| WO | 2014050879 | 4/2014 |
| WO | 2014191460 | 12/2014 |
| WO | 2015063097 | 5/2015 |
| WO | 2015186723 | 12/2015 |
| WO | 2015192117 | 12/2015 |
| WO | 2017094886 | 6/2017 |
| WO | 2017097708 | 6/2017 |
| WO | 2018014712 | 1/2018 |
| WO | 2018014960 | 1/2018 |
| WO | 2018075229 | 4/2018 |
| WO | 2018085576 | 5/2018 |
| WO | 2018088980 | 5/2018 |
| WO | 2018208724 | 11/2018 |
| WO | 2019114463 | 6/2019 |
| WO | 2019191510 | 10/2019 |
| WO | 2019217241 | 11/2019 |
| WO | 2020014074 | 1/2020 |
| WO | 2020014613 | 1/2020 |
| WO | 2020028177 | 2/2020 |
| WO | 2020069232 | 4/2020 |
| WO | 2021022193 | 2/2021 |
| WO | 2021056018 | 3/2021 |
| WO | 2021116449 | 6/2021 |
| WO | 2021168481 | 8/2021 |
| WO | 2021231684 | 11/2021 |
| WO | 2021252318 | 12/2021 |
| WO | 2021252319 | 12/2021 |
| WO | 2021252320 | 12/2021 |
| WO | 2022217193 | 10/2022 |
| WO | 2022258572 | 12/2022 |

OTHER PUBLICATIONS

Aleman, Andrea C., et al.,, "Reading and Myopia: Contrast Polarity Matters," Scientific Reports, 8 pages (2018).

Arden, G.B., et al., "Does dark adaptation exacerbate diabetic retinopathy? Evidence and a linking hypothesis," Vision Research 38:1723-1729 (1998).

Arden, GB, et al., "Regression of eariy diabetic macular edema is associated with prevention of dark adaptation", in Eye, (2011). 25, pp. 1546-1554.

Benavente-Perez, A., et al., "Axial Eye Growth and Refractive Error Development Can Be Modified by Exposing the Peripheral Retina to Relative Myopic or Hyperopic Defocus," Invest Ophthalmol Vis Sci., 55:6765-6773 (2014).

Bonar, Jr, et al, "High brightness low power consumption microLED arrays", in SPIE DigitalLibrary.org/conference-proceedings-of-spie, SPIE OPTO, 2016, San Francisco, California, United States, Abstract Only.

Carr, Brittany J., et al., "The Science Behind Myopia," retrieved from https://webvision.med.utah.edu/book/part-xvii-refractive-errors/the-science-behind-myopia-by-brittany-j-carr-and-william-k-stell/, 89 pages (2018).

Chakraborty, R., et al., "Diurnal Variations in Axial Length, Choroidal Thickness, Intraocular Pressure, and Ocular Biometrics," IOVS, 52(8):5121-5129 (2011).

Chakraborty, R., et al., "Hyperopic Defocus and Diurnal Changes in Human Choroid and Axial Length," Optometry and Visual Science, 90(11):1187-1198 (2013).

Chakraborty, R., et al., "Monocular Myopic Defocus and Daily Changes in Axial Length and Choroidal Thickness of human Eyes," Exp Eye Res, 103:47-54 (2012).

Cook, Colin A., et al., "Phototherapeutic Contact Lens for Diabetic Retinopahty," 2018 IEEE Micro Electro Mechanical Systems, pp. 62-65, XP033335512, (Jan. 21, 2018).

Cooper, J., et al., "Current status of the development and treatment of myopia", Optometry, 83:179-199 (2012).

Cooper, J., et al., "A Review of Current Concepts of the Etiology and Treatment of Myopia," Eye & Contact Lens, 44(4):231-247 (Jul. 2018).

Demory, B., et al., "Integrated parabolic microlenses on micro LED color pixels", in Nanotechnology, (2018); 29, 16, pp. 1018, Abstract Only.

Dolgin, Elie, "The Myopia Boom," Nature 519:276-278 (2015).

Edrington, Timothy B., "A literature review: The impact of rotational stabilization methods on toric soft contact lens performance," Contact Lens & Anterior Eye, 34:104-110 (2011).

Flitcroft, D.I., "The complex interactions of retinal, optical and environmental factors in myopia aetiology," 31 (6):622-660 (2012).

Garner, L.F., et al., "Crystalline Lens Power in Myopia," Optometry and Vision Science, 69:863-865 (1992).

Gwiazda, Jane, "Treatment Options for Myopia," retrieved from https://www.ncbi.nlm.nih.gov/pmc/articles/PMC2729053/, Optom Vis Sci., 86(6):624-628 (Jun. 2009).

Gwiazda, Jane, et al., "A Randomized Clinical Trial of Progressive Addition Lenses versus Single Vision Lenses on the Progression of Myopia in Children", Invest Ophthalmol Vis Sci, 44:1492-500 [PubMed: 12657584] (2003).

Haglund, Erik, et al., "Multi-wavelength VCSEL arrays using high-contrast gratings," Proc. of SPIE vol. 10113, 7 pages (2017).

Hammond, D.S., et al., "Dynamics of active emmetropisation in young chicks—influence of sign and magnitude of imposed defocus" Ophthalmic Physiol Opt. 33:215-222 (2013).

Henry W., "MicroLED Sources enable diverse ultra-low power applications", in Photonic Spectra, 2013.

Jayaraman, V., et al., "Recent Advances in MEMS-VCSELs for High Performance Structural and Functional SS-OCT Imaging,"

(56) References Cited

OTHER PUBLICATIONS

Proc. of SPIE vol. 8934, retrieved from http://proceedings.spiedigitallibrary.org/ on Dec. 1, 2015 (2014).
Jones, D., "Measure Axial Length to Guide Myopia Management," Review of Myopia Management, 5 pages (Apr. 9, 2020).
Kur, Joanna, et al., "Light adaptation does not prevent early retinal abnormalities in diabetic rats," Scientific Reports, 8 pages (Feb. 8, 2016).
Lagreze, Wolf A., et al., "Preventing Myopia," retrieved from https://www.ncbi.nlm.nih.gov/pmc/articles/PMC5615392/, Disch Arztebl Int., 114(35-36):575-580 (Sep. 2017).
Lam, Carly Siu Yin, et al., "Defocus Incorporated Multiple Segments (DIMS) spectacle lenses slow myopia progression: a 2-year randomised clinical trial," Br. J Ophthalmol. 0:1-6 (2019).
Leo, Seo-Wei, et al., "An evidence-based update on myopia and interventions to retard its progression," J AAPOS, 15 (2):181-189 (Apr. 2011).
Lingley, A.R., et al, : A single pixel wireless contact lens display, in J Micromech. Microeng., 2011; 21, 125014; doi:10.1088/0960-1317/21/12/125014, Abstract Only.
Martin, J.A., et al., "Predicting and Assessing Visual Performance with Multizone Bifocal Contact Lenses," Optom Vis Sci, 80(12):812-819 (2003).
Matkovic, K., et al., "Global Contrast Factor—a New Approach to Image Contrast," Computational Aesthetics in Graphics, Visualization and Imaging, 9 pages (2005).
McKeague C, et al. "Low-level night-time light therapy for age-related macular degeneration (ALight): study protocol for a randomized controlled trial", in Trials 2014, 15:246, http://www.trialsjournal.com/content/15/1/246.
Moreno, I, "Creating a desired lighting pattern with an LED array" in Aug. 2008, Proceedings of SPIE—The International Society for Optical Engineering 7058, DOI: 10.1117/12.795673.
Moreno, I., "Modeling the radiation pattern of LEDS", in Optics Express, 2008; 16, 3 pp. 1808.
Nickla, Debora L., et al., "Brief hyperopic defocus or form deprivation have varying effects on eye growth and ocular rhythms depending on the time-of-day of exposure," Exp Eye Res. 161:132-142 (Aug. 2017).
Ramsey, DJ, and Arden, GB, "Hypoxia and dark adaptation in diabetic retinopathy: Interactions, consequences and therapy", in Microvascular Complications-Retinopathy (JK Sun, ed.), Cur Dab Rep (2015) 15: 118, DOI 10.1007/s11892-015-0686-2, Abstract Only.
Read, Scott A., et al., "Choroidal changes in human myopia: insights from optical coherence tomography imaging," Clin Exp Optom, 16 pages (2018).
Read, Scott A., et al., "Human Optical Axial Length and Defocus," IOVS, 51(12):6262-6269 (2010).
Shivaprasad, S, et al., "Clinical efficacy and safety of a light mask for prevention of dark adaptation in treating and preventing progression of early diabetic macular oedema at 24 months (Cleopatra): a multicentre, phase 3, randomised controlled trial," in www.thelancet.com/diabetes-endocrinology vol. 6, pp. 382-391 ( May 2018).
Smith, III, Earl L., "Optical treatment strategies to slow myopia progression: Effects of the visual extent of the optical treatment zone," retrieved from https://www.ncbi.nlm.nih.gov/pmc/articles/PMC3624048/, Exp Eye Res., 114:77-88 (Sep. 2013).
Srinivasan, S., "Ocular axes and angles: Time for better understanding," J. Cataract Refract. Surg., 42:351-352 (Mar. 2016).
Torii, Hidemasa, et al., "Violet Light Exposure Can Be a Preventive Strategy Against Myopia Progression," EBioMedicine 15:210-219 (2017).
Wallman, Josh, et al., "Homeostasis of Eye Growth and the Question of Myopia," Neuron, 43:447-468 (2004).
Wolffsohn, James A., et al., "Impact of Soft Contact Lens Edge Design and Midperipheral Lens Shape on the Epithelium and Its Indentation With Lens Mobility," IOVS, 54(9):6190-6196 (2013).
Brennan NA, Toubouti YM, Cheng X, Bullimore MA. Efficacy in myopia control. Prog Retin Eye Res. Jul. 2021; 83:100923. Epub Nov. 27, 2020.
Walline JJ, Lindsley K, Vedula SS, Cotter SA, Mutti DO, Twelker JD. Interventions to slow progression of myopia in children. Cochran Database Syst Rev. Dec. 7, 2011; (12):CD004916.
Zhou WJ, Zhang YY, Li H, Wu YF, Xu J, Lv S, Li G, Liu SC, Song SF. Five-year progression of refractive errors and incidence of myopia in school-aged children in western China. J Epidemiol. Jul. 5, 2016; 26(7):386-95. Epub Feb. 13, 2016.

METHODS FOR THE TREATMENT OF REFRACTIVE ERROR USING ACTIVE STIMULATION

RELATED APPLICATIONS

This application is a continuation of U.S. patent application Ser. No. 17/650,266, filed Feb. 8, 2022 now U.S. Pat. No. 11,467,423, issued Oct. 11, 2022, which is a continuation of U.S. patent application Ser. No. 17/303,889, filed Jun. 9, 2021, now U.S. Pat. No. 11,281,022, issued Mar. 22, 2022, which claims the benefit under 35 U.S.C. § 119(e) of U.S. Provisional Patent Application No. 63/037,504, filed Jun. 10, 2020, the disclosures of which are incorporated, in their entirety, by this reference.

BACKGROUND

Myopia, also known as near-sightedness, is a visual disorder that is frequently progressive and worsens through adolescence and early adulthood. It is characterized by the ability to see objects clearly at nearer distances, but at farther distances objects become blurry. This is primarily the result of the eye being a non-spherical shape and instead being elongated, so that images of objects are not focused at the retina. In some myopic persons, the axial dimension or axis of the eye increases over time, with the result of worsening near-sightedness. The elongated dimension of the eye is commonly referred to as its axial length and is measured along the primary visual axis.

It has been demonstrated that the progression of myopia in some patients can be slowed or stopped by providing stimuli consisting of an image that is defocused in front of the retina, a technique referred to as myopic defocus. Some prior approaches for providing such stimuli rely on passive manipulation of light from the surrounding environment. However, this approach can lead to less than ideal visual results and degraded image quality in at least some instances. One approach that has been suggested involves the projection of stimulus or stimuli into the mid peripheral area of the retina, where the stimulus image is then myopically defocused. However, at least some of the prior approaches can be somewhat more complex and less than ideally suited for use with vision devices such as spectacles. Also, at least some of the prior approaches have been somewhat more cumbersome for the user to wear in at least some instances.

In light of the above improved methods and apparatus are needed that ameliorate at least some of the aforementioned limitations of the prior approaches.

SUMMARY

Embodiments of the present disclosure are directed to apparatuses and methods for an active projection system for use in the treatment of refractive error that may be incorporated into spectacles, contact lenses, or provided as an add-on layer or film to existing spectacles or lenses. The disclosed active projection system may also be incorporated into a virtual or augmented reality device, smartphone, handheld device, tablet computer, electronic game console, or similar device.

In some embodiments, an apparatus for an active projection system for treatment of refractive error comprises a plurality of projection modules and a plurality of optical elements. Each projection module generates a stimulus that is directed to an optical element which then directs the stimulus to a desired location in a person's eye. In some embodiments, the stimulus creates an image that is defocused in front of or behind the person's retina and can assist in slowing or stopping the progression of myopia in the person. Although this disclosure will generally discuss the treatment of myopia, it should be understood that the apparatuses and methods described herein may be used to treat other forms of refractive error by forming an stimulus image anterior or posterior to a peripheral region of a retina of the eye.

In some embodiments, each projection module includes a source of illumination, a stimulus forming element that generates a stimulus when illuminated by the source of illumination, and a guide that directs the generated stimulus to an optical element. The optical element directs the generated stimulus to a desired region or location of a person's eye where the stimulus forms an image that is defocused on the retina. Depending on the type of refractive error being treated, the region or location of the eye may be anterior or posterior to a peripheral region of the retina of the eye.

In some embodiments, the stimulus forming element may be a mask, film, or reticle. In some embodiments, the guide may be a lightguide and may include one or more mirrors, partial mirrors, beam splitters, or lenses to properly direct the stimulus to an optical element. In some embodiments, the guide may direct the stimulus to a facet of a lens, with the facet then directing the stimulus to, or focusing the stimulus on, an optical element.

In some embodiments, the optical element may comprise one or more mirrors, partial mirrors, beam splitters, or lenses that direct the stimulus into the eye to form an image of the stimulus at the desired location. The mirrors can be sized and shaped in many ways and may comprise one or more of flat mirrors, curved mirrors, concave mirrors, convex mirrors, spherically shaped mirrors or aspheric mirrors. In some embodiments, the optical element may comprise a lightguide that contains the one or more mirrors, partial mirrors, beam splitters, or lenses.

In some embodiments, the projection modules and optical elements may be fabricated as part of a pair of spectacles (typically as part of the frames and/or lenses), as part of a pair of contact lenses, or as a film or layer to be applied to an existing contact lens or set of spectacle lenses.

In some embodiments, the projection modules and optical elements may be incorporated into a virtual or augmented reality device, smartphone, handheld device, tablet computer, electronic game console, or similar device. In these embodiments, the projection modules and optical elements may be incorporated into an existing device or provided as an add-on or peripheral device.

In embodiments, the present disclosure is directed to an apparatus to treat refractive error of an eye, where the apparatus comprises an optic, a plurality of projection modules arranged around a periphery of the optic, and a plurality of optical elements arranged on the optic. Each of the plurality of projection modules generates and directs light to form a stimulus, typically by illuminating a mask or reticle. The plurality of optical elements receives the light from the plurality of projection modules and direct the received light to form an image of the stimulus anterior or posterior to a peripheral region of a retina of the eye.

In some embodiments, the optic comprises one of a lens in a pair of spectacles, a contact lens, or a film or layer that may be applied to, formed on, or attached to a lens. In these embodiments, the optical elements direct the received light through the lens, with the lens directing the light to form an image of the stimuli inside the eye.

In some embodiments, the optic comprises a lens with a clear central optical zone to provide a clear image to the macula while the stimuli are provided to the peripheral retina.

In some embodiments, each of the projection modules includes circuitry for activating a source of illumination in response to a control signal, a stimulus forming element that forms a stimulus when illuminated by the source of illumination, and a guide element that directs light from the stimulus forming element to at least one of the plurality of optical elements.

In some embodiments, the source of illumination comprises one or more of a LED, OLED, a phosphorescent LED or a plurality of LEDs.

In some embodiments, the guide element is a lightguide and includes a light channel to transmit light, a reflective element to redirect the transmitted light to form the image, and a focusing element to receive the redirected light and to project the redirected light toward at least one of the optical elements. In some embodiments, the lightguide has a round cross-section. In another embodiment, the lightguide has a rectangular or other suitable cross-section.

In some embodiments, each of the of optical elements includes one or more mirrors, partial mirrors, or beam splitters. In some embodiments each of the optical elements comprises a lightguide, where the lightguide includes a mirror or mirrors to redirect the received stimulus into the eye to form a stimulus image anterior or posterior to a peripheral region of the retina. Alternatively or in combination, the lightguide may comprise one or more partial mirrors or beam splitters, where the partial mirrors or beam splitters provide stimulus images of substantially same luminance to be formed by each lightguide.

The mirrors can be sized and shaped in many ways and may comprise one or more of flat mirrors, curved mirrors, concave mirrors, convex mirrors, spherically shaped mirrors or aspheric mirrors. In some embodiments, the mirror or partial mirrors comprise flat mirrors. In some embodiments, the mirror or partial mirrors comprise concave mirrors.

In some embodiments, the guide element directs light to a facet of a lens, with the facet directing the light to an optical element.

In some embodiments, the formed image of the stimulus is an illuminated cross on a dark background and optionally a white cross on a black background.

In some embodiments, the optic comprises a lens of a pair of spectacles and each of the projection modules is supported by a frame of the spectacles, and optionally are embedded or partially embedded in the frame.

In some embodiments, the optic comprises an optical substrate having a curvature substantially the same as the front curvature of a lens of a pair of spectacles and is configured to fit over the lens of the pair of spectacles. In some embodiments, the optic comprises an optical substrate having a curvature substantially the same as the back curvature of a lens of a pair of spectacles and the optic configured to fit behind the lens of the pair of spectacles. In some embodiments, the optical substrate may comprise a film or layer and will have sufficient flexibility to be fit to the front or back of the lens. Alternatively or in combination, the optical substrate may comprise a stiff substrate such as a rigid substrate, in which the substrate comprises a curvature corresponding to the front or back curvature of the lens to fit the curved surface of the lens. The curvature corresponding to the front or back curvature of the lens may comprise one or more of a spherical curvature, a toroidal curvature or a cylindrical curvature In some embodiments, a method of manufacturing an apparatus for treating refractive error of an eye includes arranging a set of projection modules around a periphery of an optic, where each of the projection modules generates and directs light to form a stimulus and arranging a set of optical elements on the optic to receive the light from the projection modules. The optical elements direct the received light to form an image of the stimulus anterior or posterior to a peripheral region of a retina of the eye.

In some embodiments, a method of correcting refractive error of an eye includes generating a stimulus by operating a set of projection modules arranged around a periphery of an optic, where each of the projection modules operates to generate and direct light to form the stimulus. The method also includes forming an image of the stimulus anterior or posterior to a peripheral region of a retina of the eye by directing light from the projection modules to a set of optical elements arranged on the optic. In this embodiment, the optical elements receive the light from the projection modules and direct the received light to form the image of the stimulus.

INCORPORATION BY REFERENCE

All patents, applications, and publications referred to and identified herein are hereby incorporated by reference in their entirety and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which.

DETAILED DESCRIPTION

Figure 1A:
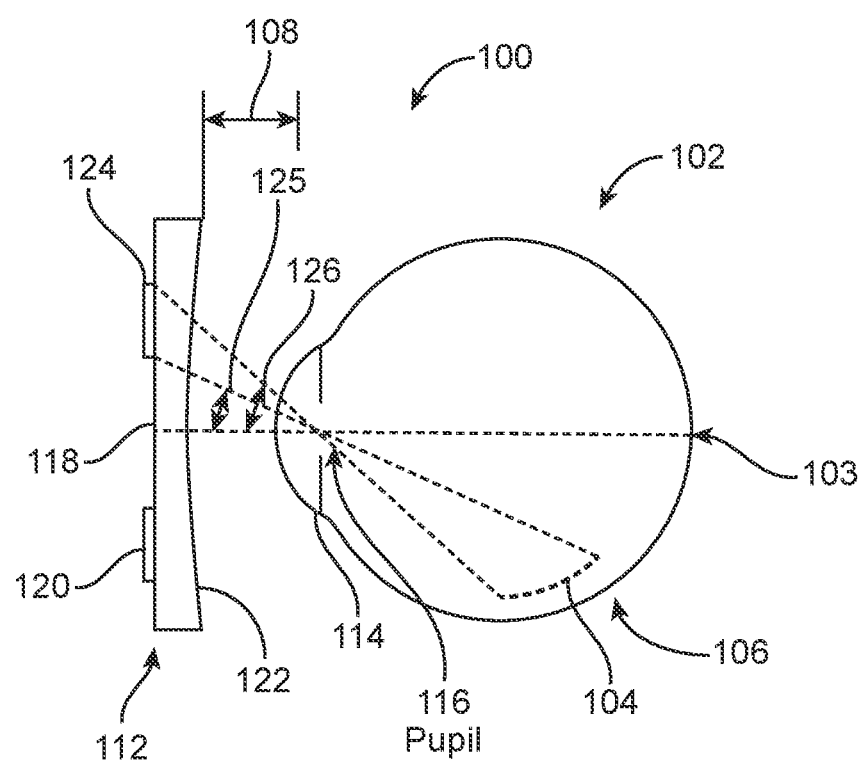
FIG. 1A shows a cross section of a vision apparatus to treat myopia or other refractive error of an eye, in accordance with some embodiments.

The following detailed description provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

Unless indicated otherwise, each of the described embodiments comprises one or more projection modules and one or more optical elements. Each projection module comprises a source of illumination, a stimulus forming element, and a guide element. The guide element may comprise a light tube or lightguide. The light tube or lightguide may comprise a mirror used to direct the formed stimulus to a lens or lenses. The mirror can be sized and shaped in many ways and may comprise one or more of a flat mirror, a curved mirror, a concave mirrors, a convex mirrors, a spherically shaped mirror or an aspheric mirror. The mirror may comprise a flat mirror, a partial mirror, or concave mirror, for example. The lens or lenses of the light tube or lightguide direct and focus the stimulus to one or more of a set of optical elements. The optical elements redirect the stimulus to form an image of the stimulus anterior or posterior to a peripheral region of the retina.

The optical elements may comprise a mirror or mirrors, a partial mirror (or set of partial mirrors), a beam splitter or beam splitters, a lens or lenses, or a concave surface or surfaces. The optical elements may be embedded in, applied to, or formed on an optic or contained in a lightguide that is embedded in, applied to, or formed on the optic. The mirror can be sized and shaped in many ways and may comprise one or more of a flat mirror, a curved mirror, a concave mirror, a convex mirror, a spherically shaped mirror or an aspheric mirror. The mirror(s) may be a flat mirror, partial mirror, or a concave mirror, for example. The projection modules may be supported by, or embedded in or partially embedded in, a frame of a pair of spectacles. In these embodiments, the optical elements may be embedded in, formed on, or applied as a film or layer to a lens of the spectacles. A facet in a lens may be used to direct a stimulus provided by a projection module to an optical element. Both the projection modules and the optical elements may be incorporated in or formed on a contact lens. Further, both the projection modules and the optical elements may be incorporated in a film or layer that is applied to the front surface or back surface of a corrective lens.

The projection modules may include circuitry for operating or activating the source of illumination. The source of illumination may be a LED, OLED, a phosphorescent LED or a plurality of LEDs. The circuitry may be a printed circuit board (PCB) that implements logic to control or activate the source of illumination. The projection module may also include a source of power, such as a battery. The logic implemented by the circuitry may be implemented in the form of a processor programmed with a set of executable instructions. The stimulus forming element may comprise a mask, film, or a reticle. The image formed by the projection module and optical element may comprise an illuminated cross on a dark background and optionally a white cross on a black background.

Although specific reference is made to spectacles and contact lenses herein, the disclosed apparatus and methods are suited for use with, or incorporation into, other devices or systems. A person of ordinary skill in the art will readily appreciate how one or more of the disclosed components or elements may be implemented as part of other systems or devices, based on the teachings provided herein.

For example, the projection modules and/or optical elements may be partially or wholly incorporated into one or more of an ophthalmic device, a TV screen, a computer screen, a virtual reality ("VR") display, an augmented reality ("AR") display, a handheld device, a mobile computing device, a tablet computing device, a smartphone, a wearable device, a spectacle lens frame, a spectacle lens, a near eye display, a head-mounted display, a goggle, a contact lens, an implantable device, a corneal onlay, a corneal inlay, a corneal prosthesis, or an intraocular lens.

Although the presently disclosed methods and apparatus can be used to treat many types of refractive error, the presently disclosed methods and apparatus are well suited to treat the progression of myopia, for example.

FIG. 1A shows a cross section of a vision apparatus 100 to treat myopia or other refractive error of an eye 102, in accordance with some embodiments. The projection modules and optical elements described herein may be implemented as part of the optic 112 by use of any suitable process. Such processes include embedding, etching, film deposition, photo-lithography, insertion into a cavity, molding, etc. The images generated by the stimulus forming element described herein are transmitted through the optic 112 to the eye 102 of the user, represented by the cornea 114 and the pupil 116. The optic 112 may comprise a refractive lens that changes the focus of the light before the light enters the eye 102 of a user. The optic may instead comprise a film or layer that is applied to a lens, either to the front or back of a lens.

The optic 112 may include a posterior optical structure 122 that may be curved or otherwise shaped to adjust the focus of the stimuli onto the user's eye 102. For example, in some embodiments in which, for example, the projection modules and optical elements are implemented as part of, or as an addition to spectacles, the optic 112 may comprise a prescription lens to correct refractive errors of the patient's eye 102 with the posterior optical surface 122 shaped to correct one or more of myopia, hyperopia, astigmatism, and other refractive errors of the eye 102.

A defocus treatment device 124 may be attached to, embedded in, or formed as part of a surface of, the optic 112. For example, in FIG. 1A the defocus treatment device 124 is a part of, or attached to, the front surface of the optic 112. In some embodiments, the treatment device 124 is adhered to the optic 112 with an adhesive. In some embodiments, the defocus treatment device 124 comprises a peripheral defocus optical structure 120 arranged around a central optical zone 118. In some embodiments, the defocus optical structure 120 alters the focus of the light. The defocus optical structure can be configured to form a stimulus image 104 anterior to the retina 106 to treat refractive error of the eye 102 such as myopia. Alternatively, the defocus optical structure 120 can be configured to form an image of the stimulus 104 posterior to the retina 106 of the eye 102.

Although in some embodiments, reference is made to the treatment defocus device 120 being adhered to an optic 112 where the optic is a lens, in some embodiments the defocus optical structure 120 is formed directly on the surface of a lens, for example with structures etched into the surface of a lens. In some embodiments, the defocus optical structure 120 is formed as a module that is embedded in a lens or is formed as part of a process of molding a lens.

The dimensions of the optical zone 118 and peripheral defocus optical structure 120 zone can be configured in many ways. In some embodiments, the optical zone 118 is configured to provide a clear view of an object on the macula 103 while the peripheral defocus structure 120 provides the stimulus to the peripheral retina. In some embodiments, the peripheral defocus optical structure 120 is sized and shaped to transmit light at an angle within a range from 12 degrees to 40 degrees with reference to an entrance pupil of the eye 102 or within a range from 15 to 35 degrees, for example. In some embodiments, the angle comprises a half-angle, such as an angle between the boundary of the optical zone and a line formed through the center of the optical zone and the center of the entrance pupil. In some embodiments, the peripheral defocus optical structure 120 is sized to be at an angle within range from 15 degrees to 50 degrees with reference to an entrance pupil of the eye, for example.

In some embodiments, the peripheral defocus optical structure 120 comprises an inner boundary and an outer boundary. The inner boundary corresponding to an inner boundary angle 125 within a range from 15 degrees to 20 degrees with reference to the entrance pupil 116 of the eye 102 and the outer boundary corresponding to an outer boundary angle 126 within a range from 25 degrees to 70 degrees with reference to the entrance pupil of the eye 102. In some embodiments, the lens is a distance 108 from the eye 102. The distance, the inner boundary, and the outer boundary may be dimensioned to provide the inner angle and the outer angle with reference to the entrance pupil of the eye 102.

The peripheral defocus optical structure 120 may be annular in shape, having an inner diameter and an outer diameter selected such that the peripheral defocus is applied to a portion of the retina of the patient's eye 102 that is eccentric to the fovea. For example, the inner diameter may be at an angle of about 7.5 degrees with respect to an optical axis of the optic 112 and pupil, this angle may be referred to as an inner boundary angle 125. The outer diameter of the peripheral defocus optical structure 120 may be at an outer boundary angle 126 with respect to the optical axis of the primary eye 102 and the people, for example at 17.5 degrees. Such an arrangement, results in the peripheral defocus optical structure 120 being located in a peripheral field of view of the user with a corresponding defocus of the projected light in a peripheral region of the user's retina eccentric to the fovea.

Although reference is made to an annular shape, the peripheral defocus optical structure 120 can be configured with other shapes, such as polygons, squares, triangles, and may comprise a plurality of discrete optical structures located around the optical zone at appropriate locations.

In some embodiments, the peripheral defocus optical structure 120 may include optics or optical structures that change the focus of the light projected into a person's eye 102. Peripheral defocus optical structure 120 may comprise one or more of diffractive optics, lenslets, gradient index ("GRIN") lenslets, crossed cylindrical rods, masks, or echelettes that alter the focus of light passing through the defocus optical structure 120.

In some embodiments, the peripheral defocus optical structure 120 is dimensioned to provide defocused images to a peripheral portion of the retina. In some embodiments, the defocus optical structure 120 is configured to provide a stimulus to a peripheral portion of the retina that comprises a region of the retina outside the fovea or the macula 103, so as to provide clear vision to the fovea and the macula 103 when the user looks ahead and the peripheral defocus optical structure 120 provides a defocused image onto the peripheral retina. The image may be defocused in a range between 2.0 to 6.0 Diopters ("D") myopically or hyperopically with respect to the retina. For example, the defocus may be 3.5 D to 5 D anterior to the retina, e.g. myopic defocus, or posterior to the retina, e.g. hyperopic defocus. The defocus is preferably between 2.5 D to 5.0 D, and more preferably between 3.0 D to 5.0 D.

In some embodiments, a defocus treatment device includes use of localized stimuli projected into the peripheral zone to treat refractive errors of the eye 102. In the defocus treatment device 124, the stimuli are projected through the peripheral defocus optical structure 120 and accordingly, the stimuli are defocused by the peripheral defocus optical structure.

For the treatment of spherical refractive errors of the eye 102, such as myopia, the stimulation projected to the retina 106 may be uniform about the periphery of the central optical zone 118. For the treatment of cylindrical refractive errors of the eye 102, such as astigmatism, the stimulation projected to the retina may be non-uniform about the periphery of the central optical zone 118. For example, the stimulation may be greater along a meridian corresponding to or aligned with an astigmatic first axis of the eye 102 and symmetrically mirrored about a second astigmatic axis of the eye 102.

Embodiment 1

Figure 1B:
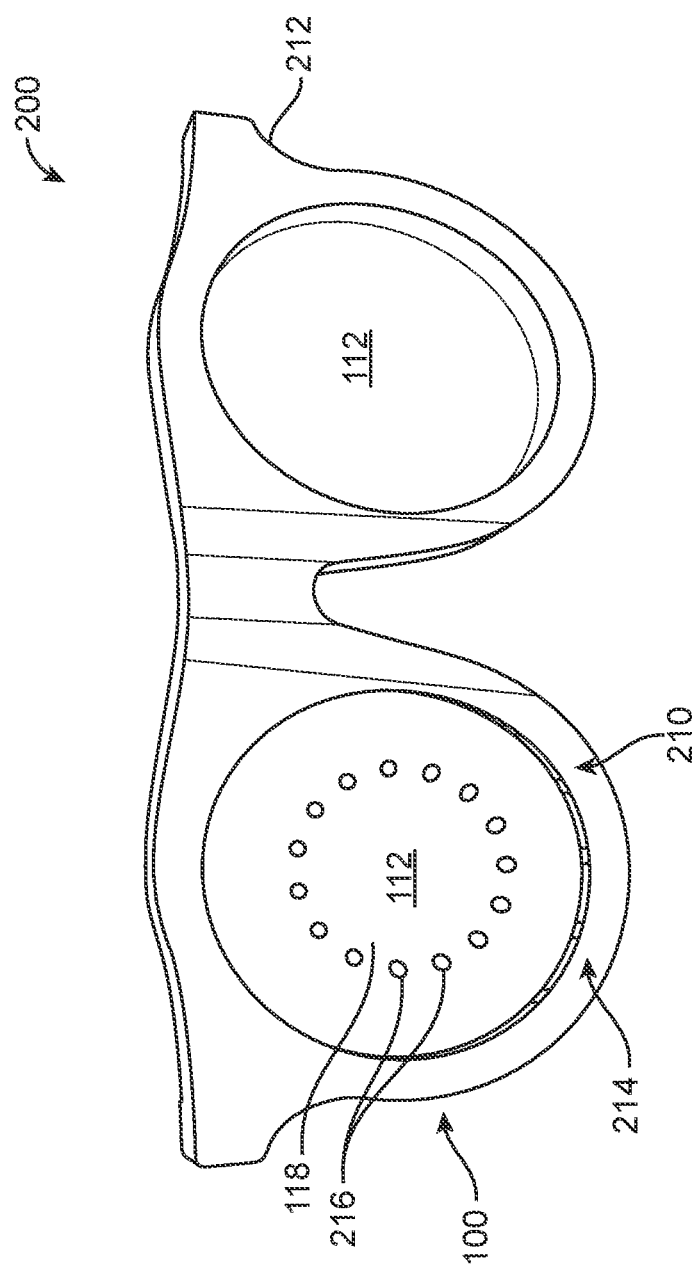
FIG. 1B shows a pair of spectacles that incorporate an apparatus for treatment of a refractive error of an eye, in accordance with some embodiments.
Figure 2:
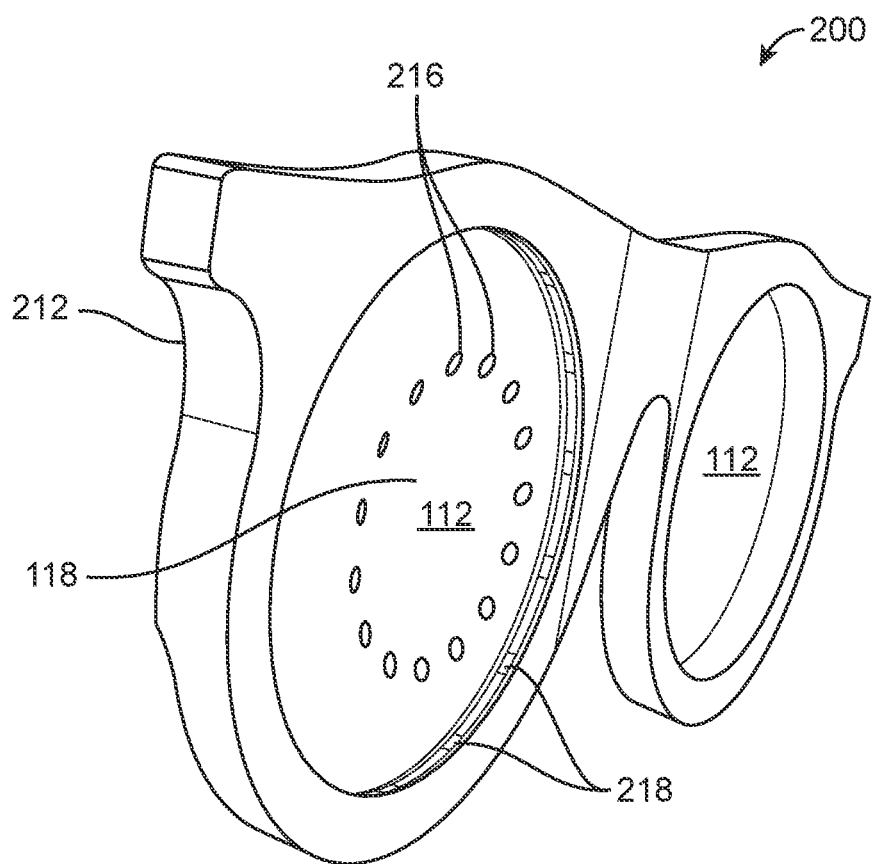
FIG. 2 shows a side view of the spectacles of FIG. 1B, in accordance with some embodiments.

FIG. 1B shows a pair of spectacles 200 that incorporate an apparatus 100 for treatment of a refractive error of an eye, in accordance with some embodiments. FIG. 2 shows a side view of the spectacles 200 of FIG. 1B, in accordance with some embodiments. As shown in FIGS. 1B and 2, some embodiments the apparatus 100 incorporates micro projection systems (termed "projection modules" herein), each with its own optics 210, that are arrayed circumferentially around the periphery of a lens or other type of optic 112 and within the frame 212 of a pair of spectacles 200. The projection modules 214 contain a light source (termed a "source of illumination" herein) with a mask or other element being illuminated to create a stimulus (termed a "stimulus forming element" herein).

The light source may comprise an LED, OLED, or other form of display. The projection module 214 may include a light tube or lightguide (termed a "guide element" herein) that directs the stimulus to an optical element. The light tube or lightguide may include a mirror which directs the formed stimulus to a set of optical elements 216 (for example, mirrors, partial mirrors, beam splitters, or lightguides) that are arranged on or in a lens 112. The optical elements 216 redirect the stimulus or image through the spectacle lens to the eye. As shown in FIG. 2, in some embodiments, a facet or facets 218 in a lens are used to transmit a stimulus or image from a projection module that is incorporated into a spectacle frame to a set of optical elements.

In some embodiments, the mirrors are configured to reflect a narrow bandwidth of light and to transmit light at other wavelengths. The reflective bandwidth can be within a range from about 5 nm to about 50 nm (or 10 nm to 25 nm) for the full width half maximum, for example, in order to transmit wavelengths outside the reflective bandwidth. This approach can provide a mirror that is substantially transparent and allow the optic, e.g. lens, to transmit light with a refraction that is substantial similarly to regions of the optic without the mirrors, e.g. the optical zone. This approach can allow the wearer to have substantially clear focused vision in the regions with the mirrors. When the projection modules are activated, the stimuli are imaged anterior or posterior to the retina and perceptible to the user. With these embodiments, the light source typically comprises a bandwidth that is typically less than the reflective bandwidth to decrease stray light, although the light source bandwidth may be greater than the bandwidth of the mirrors. The bandwidth of the plurality of light sources can be within a range from 5 nm to 50 nm, for example from 10 nm to 25 nm, for the full width half maximum of the bandwidth of the light source. In some embodiments, the mirrors comprise dichroic mirrors with one or more layers to provide an appropriate bandwidth.

Figure 3A:
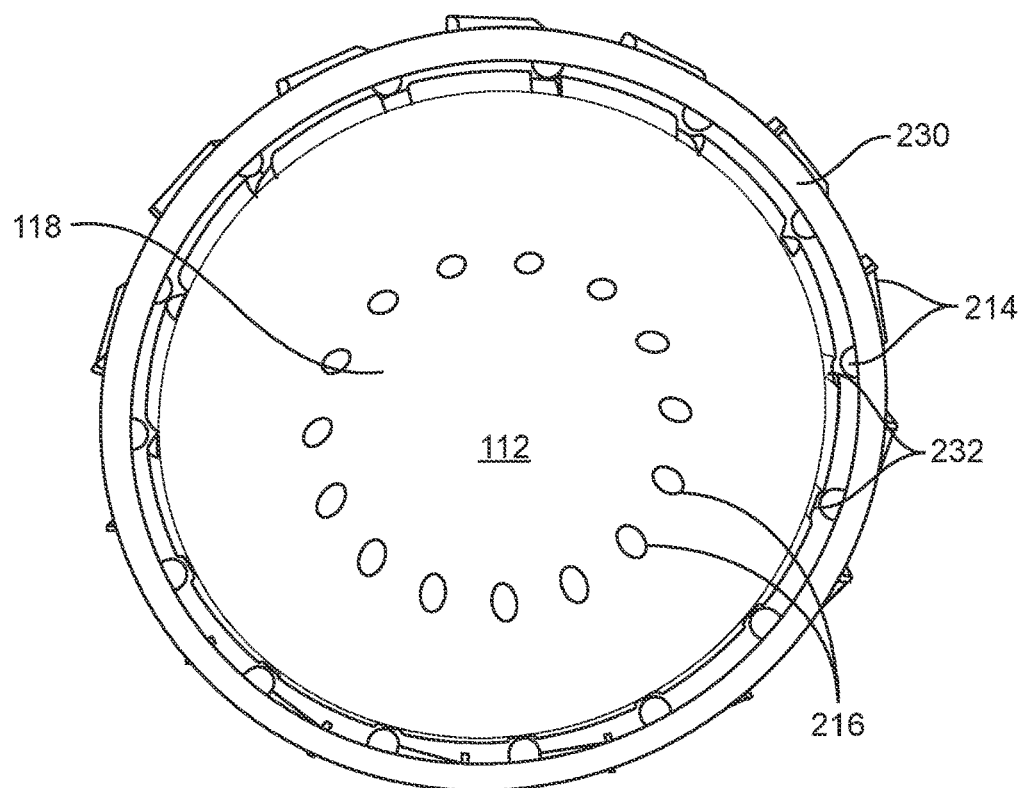
FIGS. 3A and 3B show a lens of the spectacles of FIG. 1B in which an apparatus for treatment of a refractive error of an eye has been incorporated, in accordance with some embodiments.
Figure 3B:
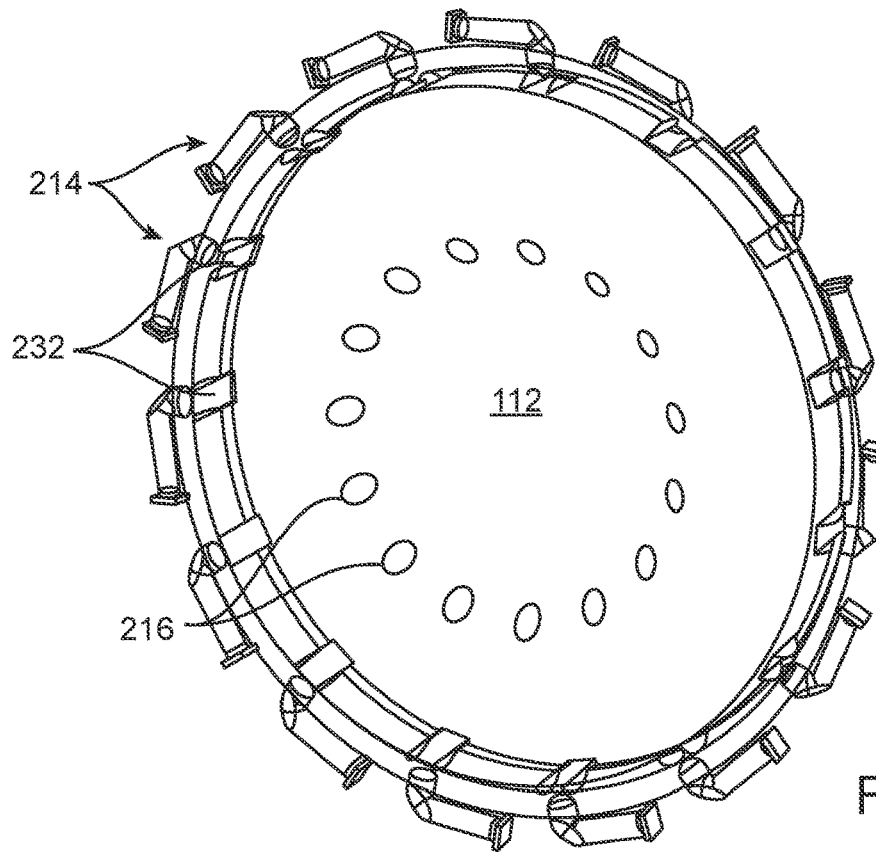

FIGS. 3A and 3B show a lens 112 of the spectacles 200 of FIG. 1B in which an apparatus 100 for treatment of a refractive error of an eye has been incorporated, in accordance with some embodiments. As shown in the figures, arranged around a periphery of the lens are a plurality of projection modules 214, where in some embodiments the projection modules may be fabricated as elements of a printed circuit board (PCB) 230. The projection modules 214 generate a stimulus that is provided to a facet 232 in the lens 112. The facet 232 acts to direct the generated stimulus to an embedded or applied optical element 216, such as a mirror, partial mirror, beam splitter, or lightguide. The optical elements 216 of FIGS. 3A and 3B are imbedded mirrors.

Figure 4A:
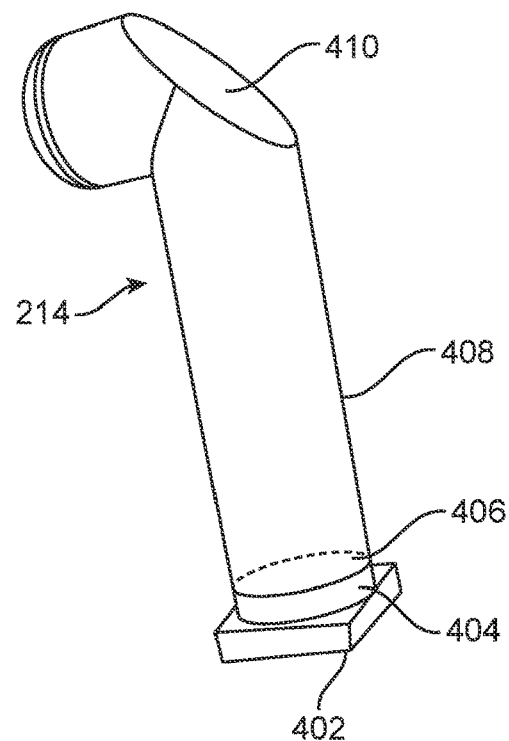
FIGS. 4A and 4B show a projection module that may be part of an apparatus for treatment of a refractive error of an eye, in accordance with some embodiments.
Figure 4B:
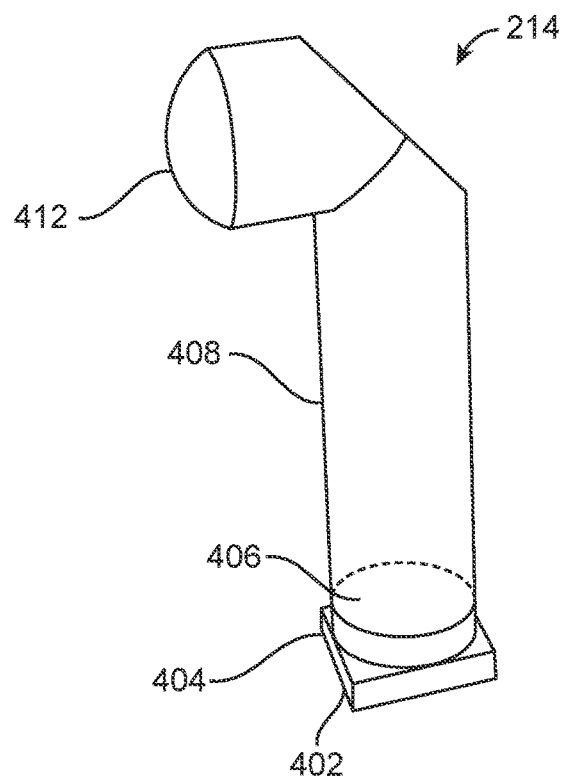

FIGS. 4A and 4B show a projection module 214 that may be part of an apparatus 100 for treatment of a refractive error of an eye, in accordance with some embodiments. As shown in FIGS. 4A and 4B, some embodiments of a projection module includes a PCB 402 (which may contain or implement circuitry, a processor, or control logic), a source of illumination 404, a mask, film, or reticle that is used to generate or form a stimulus, and a light tube or lightguide that transmits the generated stimulus to a mirror 410. In this embodiment, the mirror 410 acts to redirect the generated stimulus to a lens or lenses 412. The lens or lenses 412 of the light tube or lightguide act to direct and focus the generated stimulus to one or more optical elements 216, such as the mirrors described with reference to FIGS. 1B, 2, 3A, and 3B.

Figure 5:
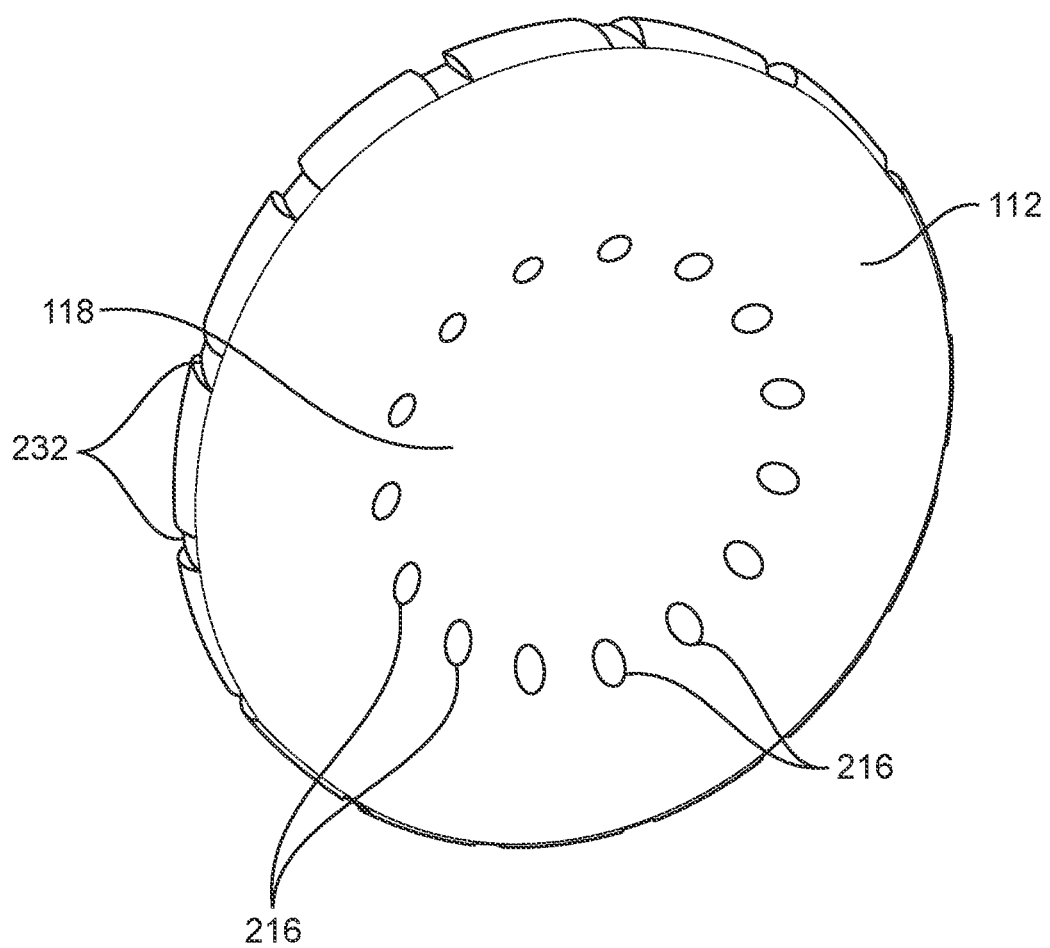
FIG. 5 shows a lens of the spectacles of FIG. 1B, including the lens facets and embedded mirrors (optical elements), in accordance with some embodiments.
Figure 6:
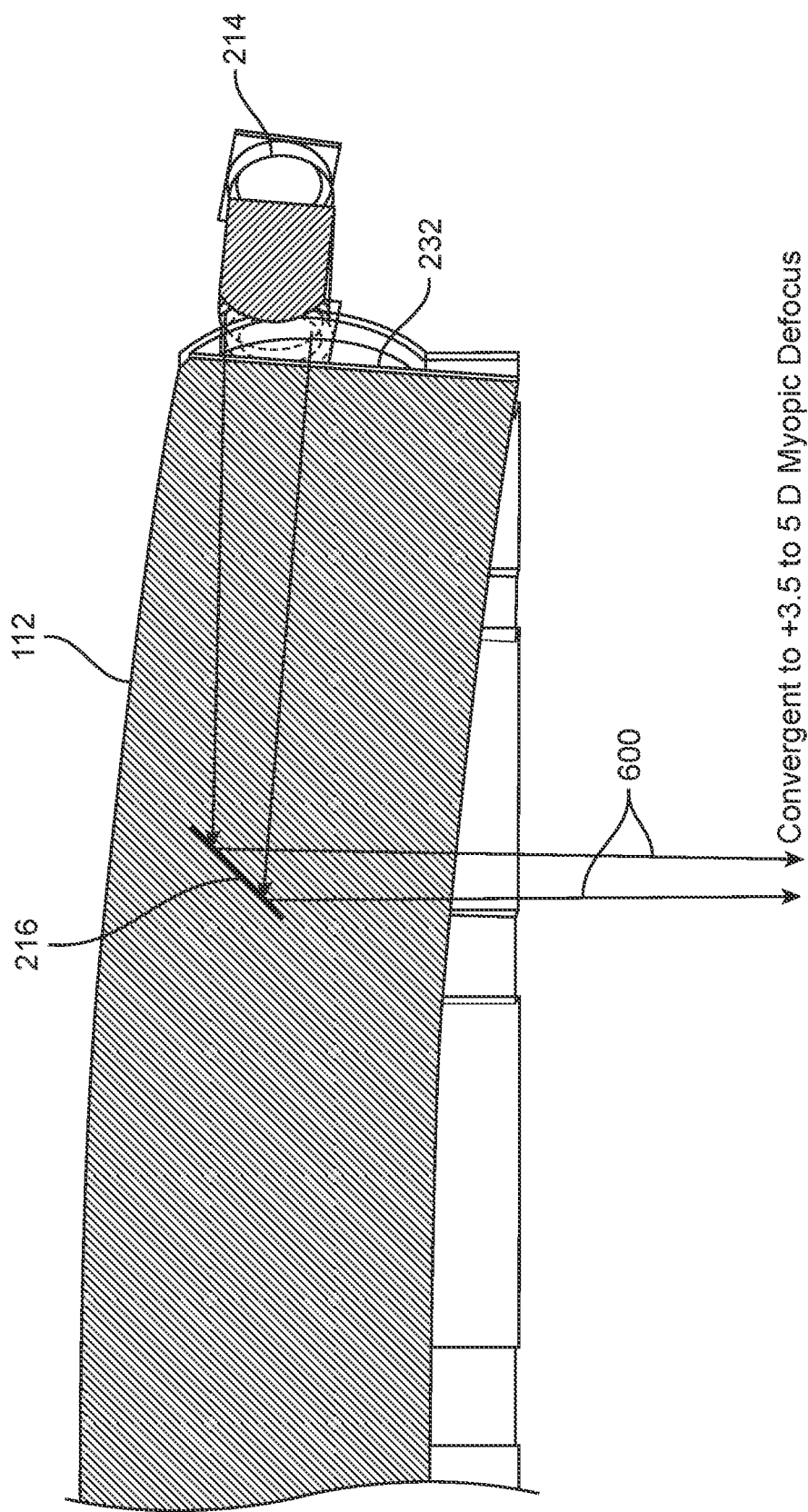
FIG. 6 shows a view of the lens of FIG. 5 and the use of a mirror embedded in the lens to redirect the light, in accordance with some embodiments.

The light tube or lightguide 408 may contain a convex surface 412, a lens, or lenses that create convergent light exiting the light tube or lightguide 408. As mentioned, in some embodiments, a facet on the edge of the spectacle lens or other lens directs the light from the projection module 214 to an optical element 216 which is embedded in, formed on, or applied to the lens. The optical element (for example, a mirror) directs the light such that it focuses an image at the appropriate location in the eye. FIG. 5 shows a lens 112 of the spectacles of FIG. 1B, including the lens facets 232 and a set of embedded mirrors 216 (i.e., the optical elements), in accordance with some embodiments. FIG. 6 shows a view of the lens of FIG. 5 and includes the use of a mirror 216 embedded in the lens 112 as an optical element to redirect the light 600, in accordance with some embodiments. As shown in the FIG. 6, a facet in the lens directs light from a projection module to the mirror.

Embodiment 2

Figure 7:
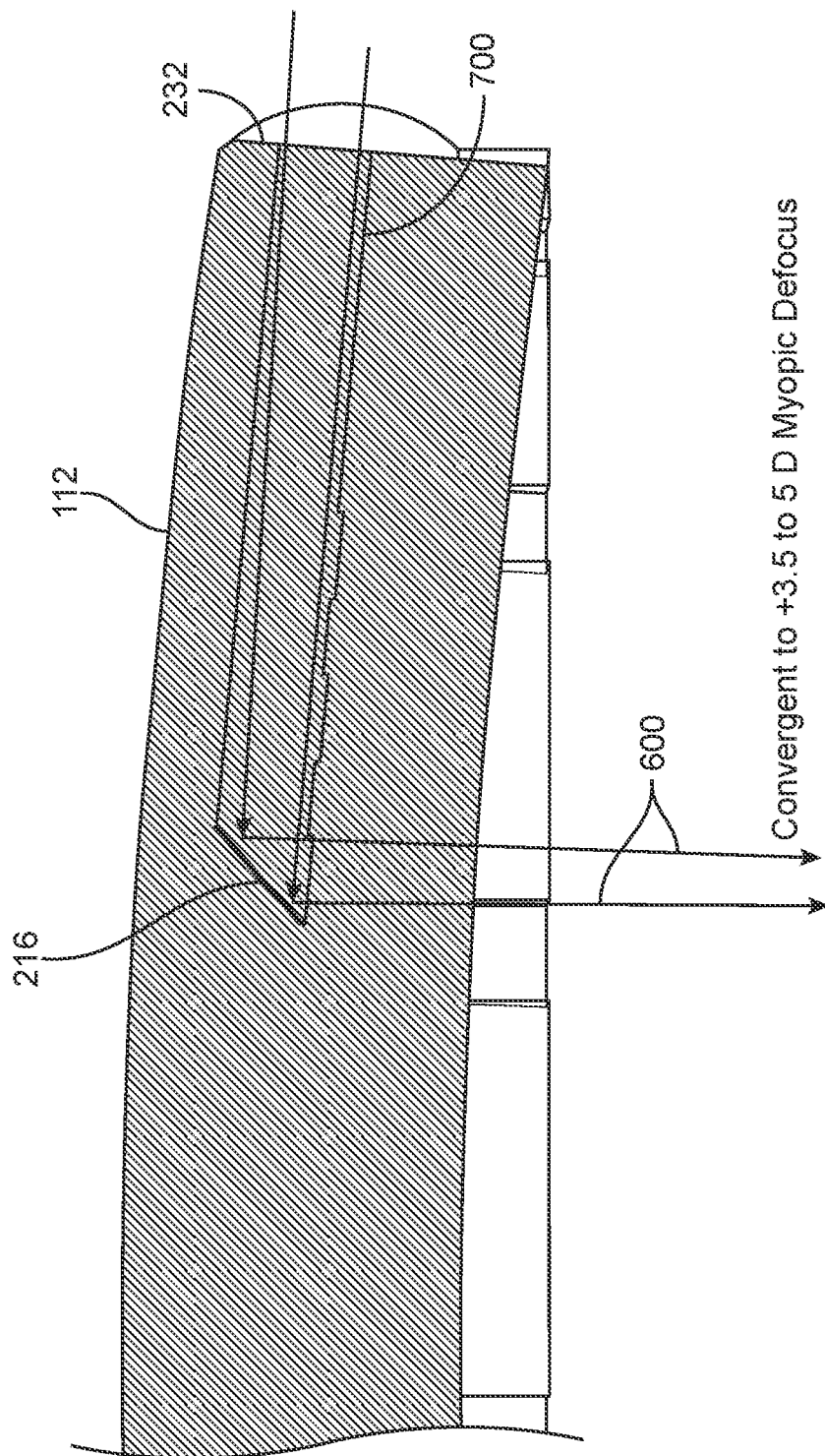
FIG. 7 shows a view of the lens of FIG. 5 and the use of a lightguide embedded in the lens and containing a mirror to redirect the light, in accordance with some embodiments.

This embodiment comprises the projection modules and optical elements described with reference to FIGS. 1B, 2, 3A, 3B, 4A, and 4B. However, in this embodiment, a facet 232 on the edge of the spectacle lens 112 directs the light 600 to a light guide 700 which includes a mirror 216. The lightguide 700 is embedded in, formed on, or applied to the lens 112 and the mirror 216 directs the light to form an image in the eye. FIG. 7 shows a view of the lens of FIG. 5 and the use of a lightguide 700 embedded in the lens and containing a mirror to redirect the light, in accordance with some embodiments. The lightguide 700 may have the properties and characteristics of lightguide 408.

Embodiment 3

Figure 8:
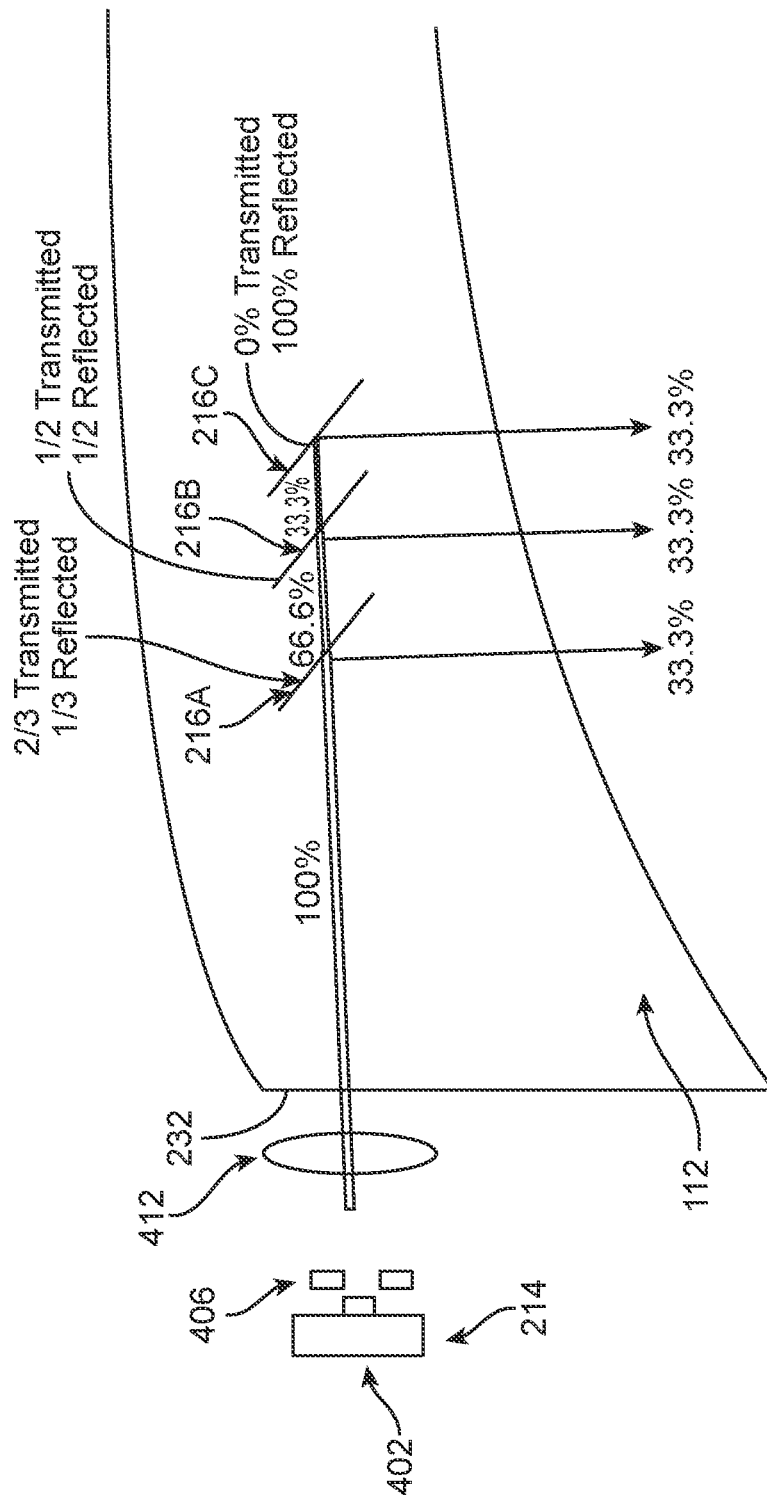
FIG. 8 shows a view of the lens of FIG. 5 and the use of a set of partial mirrors embedded in the lens to redirect the light, in accordance with some embodiments.

This embodiment comprises the projection modules and optical elements described with reference to FIGS. 1B, 2, 3A, 3B, 4A, and 4B. However, in this embodiment, a facet 232 on the edge of the spectacle lens 112 directs the light to a set of partial mirrors 216A, 216B, 216C (or beam splitters, etc.) which are embedded in, formed on, or applied to the lens 112. The light reflected by the partial mirrors 216A, 216B, 216C causes each reflection to be of the same luminance when an image is focused in the eye. FIG. 8 shows a view of the lens of FIG. 5 and the use of a set of partial mirrors embedded in the lens to redirect the light, in accordance with some embodiments.

As shown in FIG. 8, each partial mirror reflects a percentage of the incident light, while transmitting the remainder. In the example shown in FIG. 8, for the first partial mirror 216A one-third of the incident light is reflected with two-thirds of the incident light being transmitted. For the second partial mirror 216B, one-half of the incident light is reflected with one-half of the incident light being transmitted. For the third partial mirror 216C, all of the incident light is reflected with none being transmitted. Note that by configuring a set of partial mirrors or beam splitters appropriately (i.e., with the appropriate percentages or fractions of reflection and transmission relative to each other), a set of beams of light having equal luminance may be formed and directed as desired. For example, as shown in FIG. 8, each mirror reflects one third of the light provided from the projection module.

Figure 9:
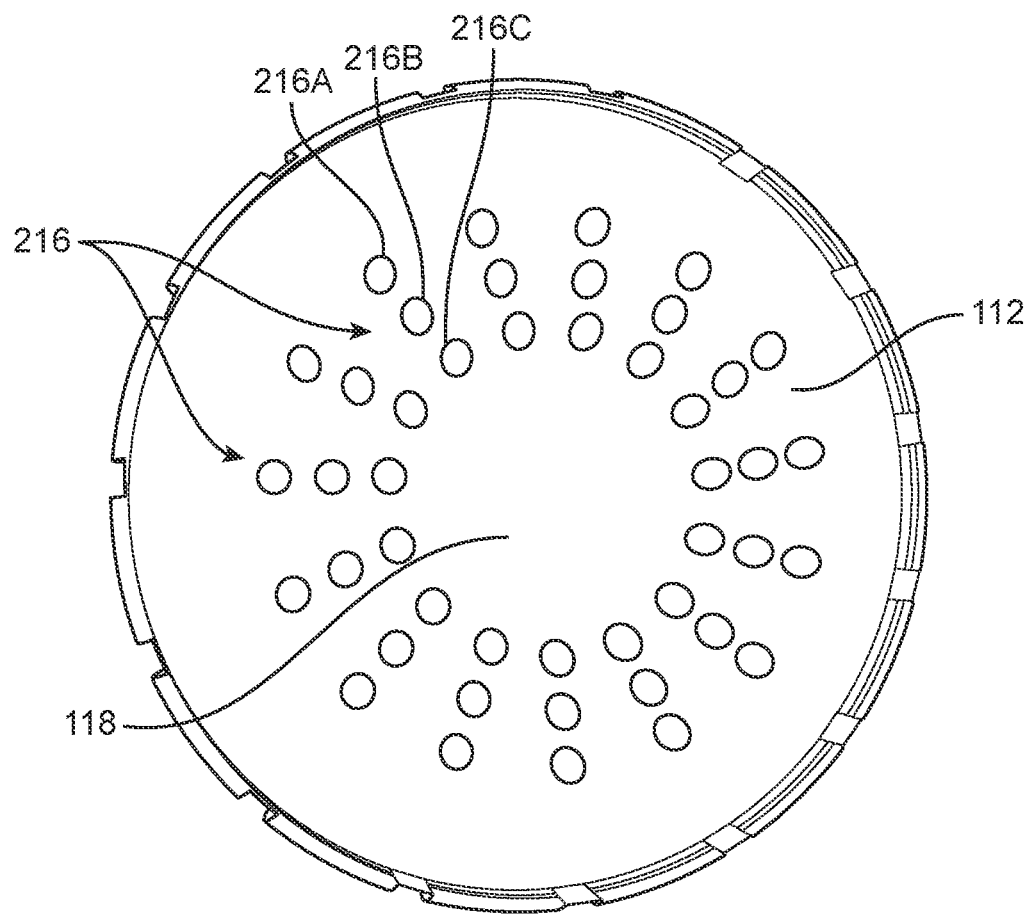
FIG. 9 shows a view of the lens of FIG. 8 with a set of partial mirrors embedded in the lens to redirect the light, in accordance with some embodiments.
Figure 10:
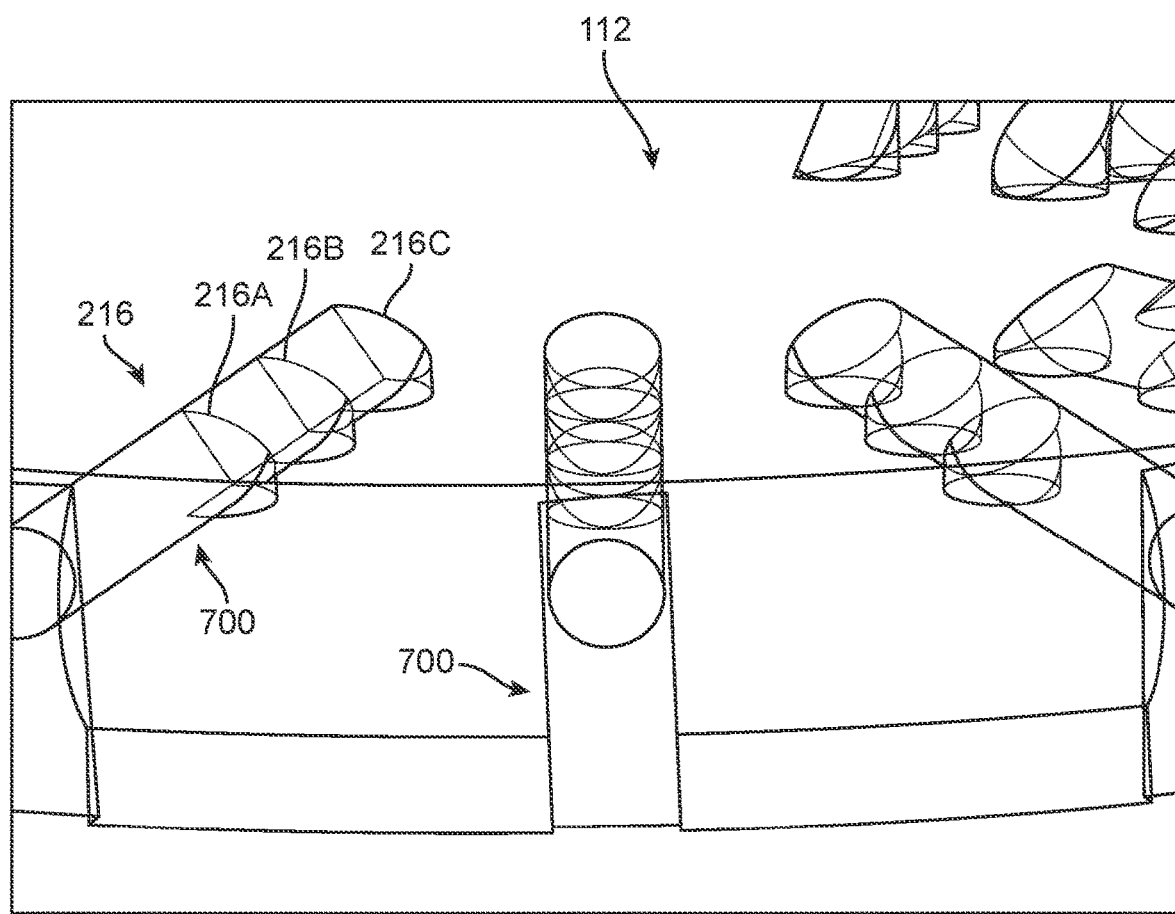
FIG. 10 shows the operation of the set of partial mirrors of FIG. 9, in accordance with some embodiments.

FIG. 9 shows a view of the lens of FIG. 5 with a set of partial mirrors 216A, 216B, 216C embedded in the lens 112 to redirect the light, in accordance with some embodiments. FIG. 10 shows the operation of the set of partial mirrors 216 of FIG. 9, in accordance with some embodiments. As shown in the figure, the luminance or intensity of the reflected light varies as the light intersects each partial mirror 216A, 216B, 216C in a set and is partially (or wholly) reflected. This behavior enables the selection of the characteristics of each partial mirror in a set to result in each set producing an image of the stimuli that is of the same luminance when viewed by the eye.

The partial mirrors 216A, 216B, 216C may be selected to have a specific reflectivity/transmissivity relationship as a function of wavelength, with the selection depending on the output of the source of illumination in the projection modules. This enables the design and implementation of a set of partial mirrors that will combine with a specific source of illumination to produce the desired equal luminance reflections.

Embodiment 4

Figure 11:
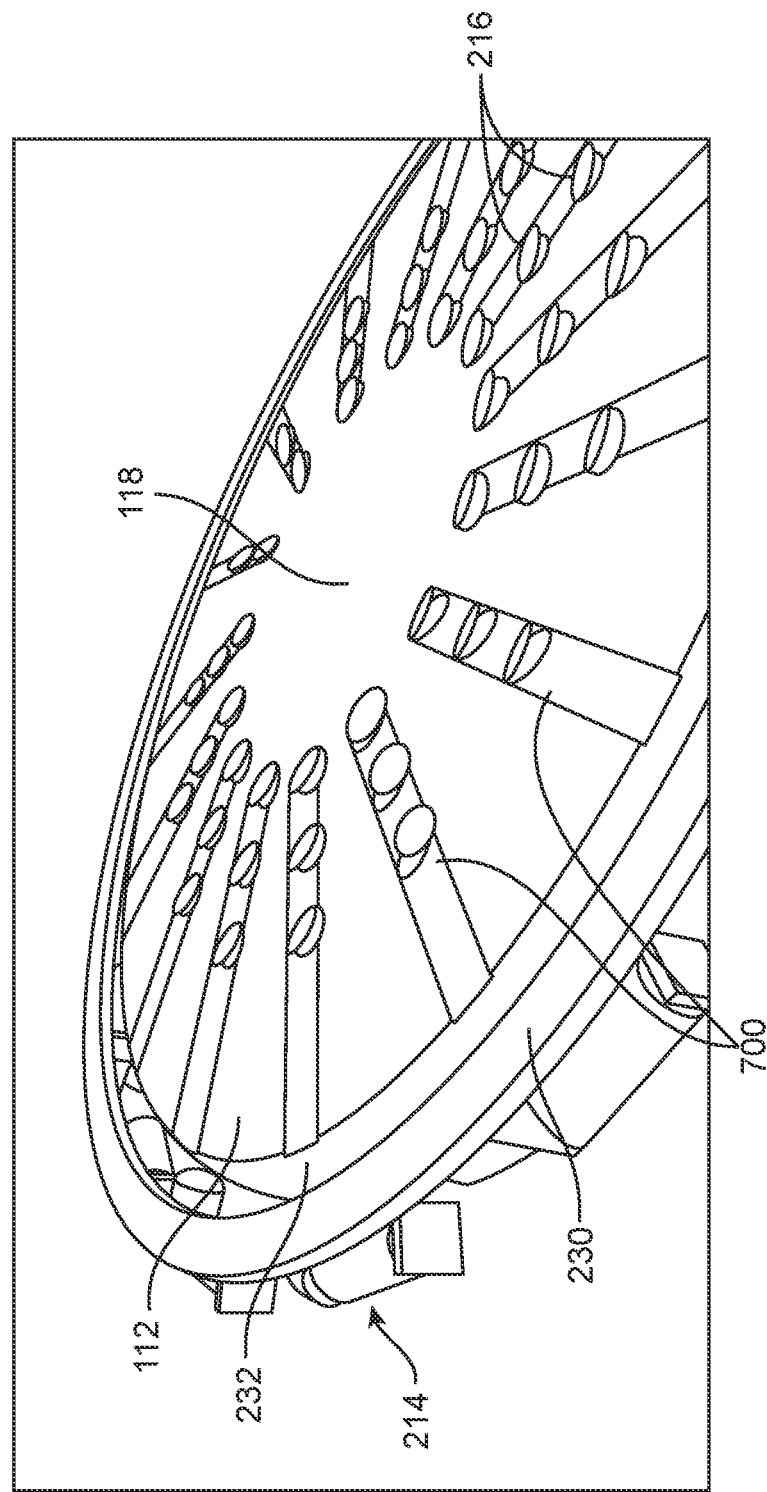
FIG. 11 shows a spectacle lens in which a facet directs light from a projection module into a lightguide, in accordance with some embodiments.
Figure 12:
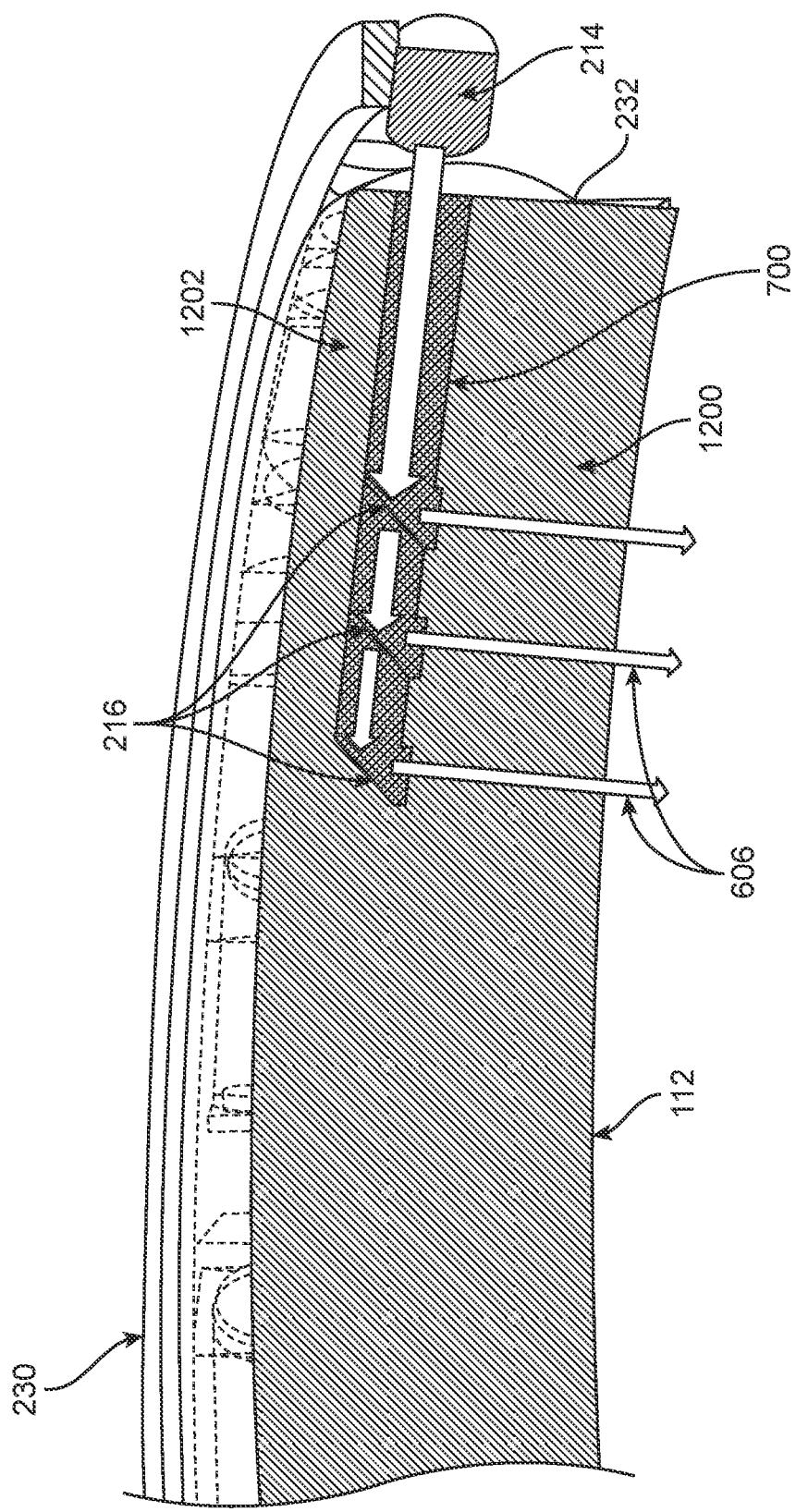
FIG. 12 shows an example of the lightguide of FIG. 11 in which a set of partial mirrors are used to reflect the light, in accordance with some embodiments.

This embodiment comprises the projection modules 214 and optical elements 216 described with reference to FIGS. 1B, 2, 3A, 3B, 4A, and 4B. However, in this embodiment, a facet 232 on the edge of the spectacle lens 112 directs the light to a lightguide 700 embedded in, formed on, or applied to the lens 112 and containing a set of partial mirrors 216 (or beam splitters). As described, the light 600 reflected by the partial mirrors 216 causes each reflection to be of the same luminance when an image is focused in the eye. FIG. 11 shows a spectacle lens in which a facet 232 directs light from a projection module 214 into a lightguide 700, in accordance with some embodiments. FIG. 12 shows an example of the lightguide 700 of FIG. 11 in which a set of partial mirrors 216 are used to reflect the light 600, in accordance with some embodiments.

In this and other embodiments, the lightguide 700 may be fabricated or manufactured using a triple molding, etching, deposition, photo-lithography or other suitable process. In such a process, a first layer 1200 or film may be deposited, molded or otherwise formed to serve as a base layer. Next, a set of partial mirrors or beam splitters 216 may be deposited, molded, or otherwise formed onto the base layer in one or more process stages. This may be accomplished by forming one partial mirror or beam splitter in each stage or forming one portion of a partial mirror or beam splitter in each stage and iteratively building the desired set. Finally, a top layer 1202 may be deposited, molded, or otherwise formed on the layer containing the partial mirrors.

Embodiments 5 A, B, C

Figure 13:
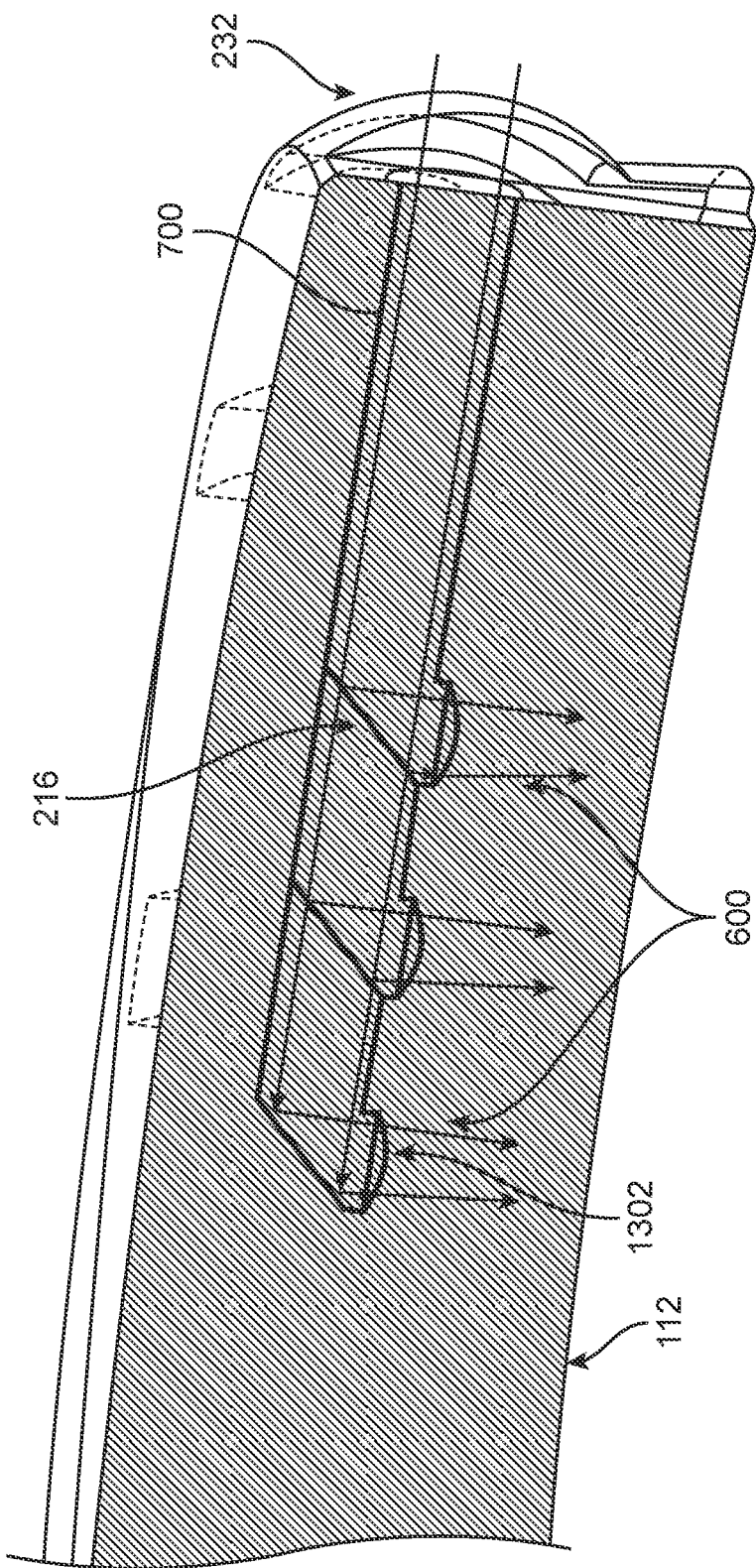
FIG. 13 shows a view of a lens in which a facet directs light from a projection module to a lightguide containing a set of mirrors which direct the light to a convex surface, in accordance with some embodiments.

These embodiments comprise the projection modules and optical elements described with reference to FIGS. 1B, 2, 3A, 3B, 4A, and 4B. However, in these embodiments, a facet 232 on the edge of the spectacle lens 112 directs the light to a mirror 216 or mirrors embedded in, formed on, or applied to the lens (which as shown in FIG. 13, may be contained in a lightguide 700). The mirror or mirrors 216 reflect the light such that it is further focused by a convex surface, lens, or lenses 1302. The convex surface, lens, or lenses 1302 are concentric with the light 600 so that the image focuses in the proper location in the eye.

Figure 14:
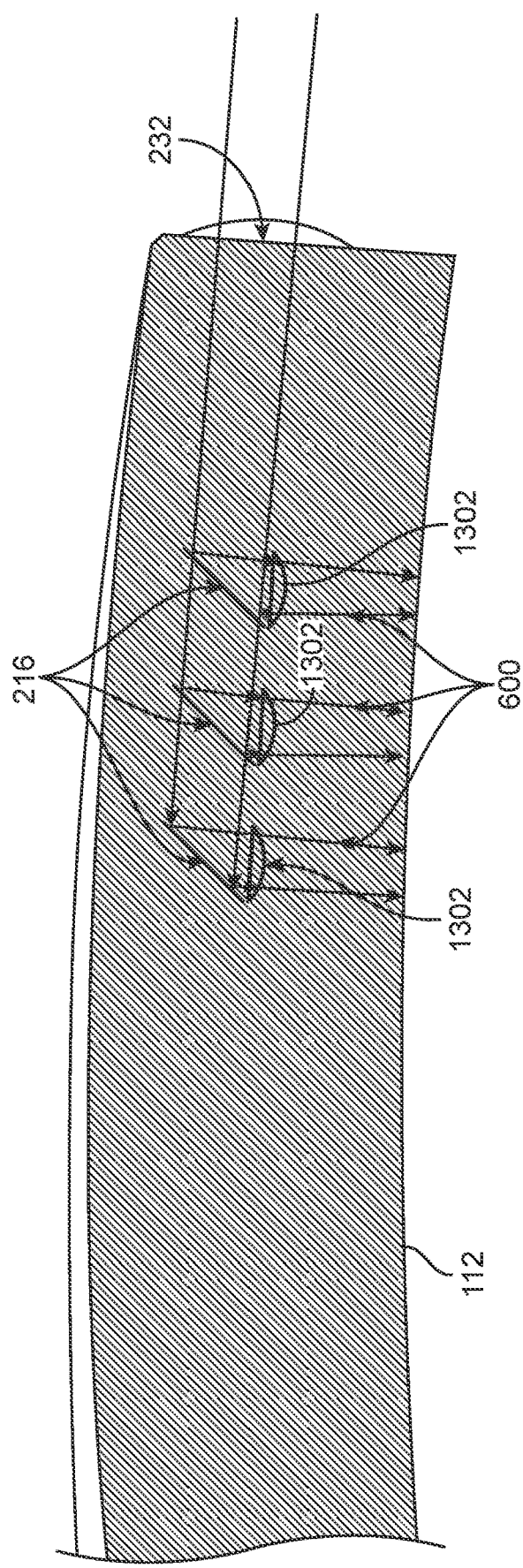
FIG. 14 shows a view of a lens in which a facet directs light from a projection module to a set of mirrors which direct the light to a convex surface, in accordance with some embodiments.
Figure 15:
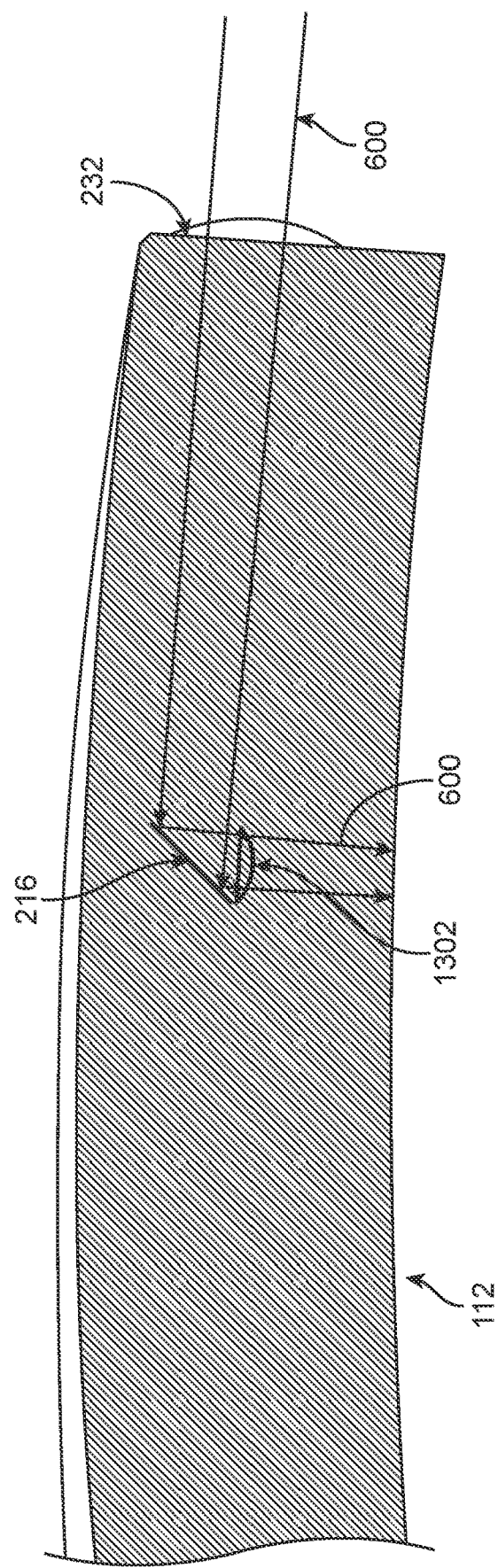
FIG. 15 shows a view of a lens in which a facet directs light from a projection module to a mirror which directs the light to a convex surface, lens, or lenses, in accordance with some embodiments.

FIG. 13 shows a view of a lens 112 in which a facet 232 directs light from a projection module to a lightguide 700 containing a set of mirrors 216 which then direct the light to a convex surface 1302, in accordance with some embodiments. FIG. 14 shows a view of a lens 112 in which a facet 232 directs light from a projection module to a set of mirrors 216 which direct the light to a convex surface 1302, in accordance with some embodiments. FIG. 15 shows a view of a lens 112 in which a facet 232 directs light from a projection module to a mirror 216 which directs the light to a convex surface, lens or lenses, 1302 in accordance with some embodiments.

Embodiments 6 A, B, C

These embodiments comprise the projection modules and optical elements described with reference to FIGS. 1B, 2, 3A, 3B, 4A, and 4B. However, in these embodiments, a facet 232 on the edge of the spectacle lens 112 directs the light 600 to a concave mirror or mirrors 1302 embedded in, formed on, or applied to the lens (and which may be contained in a lightguide). The concave mirror or mirrors 1302 reflect the light such that an image focuses in the proper location in the eye.

Figure 16:
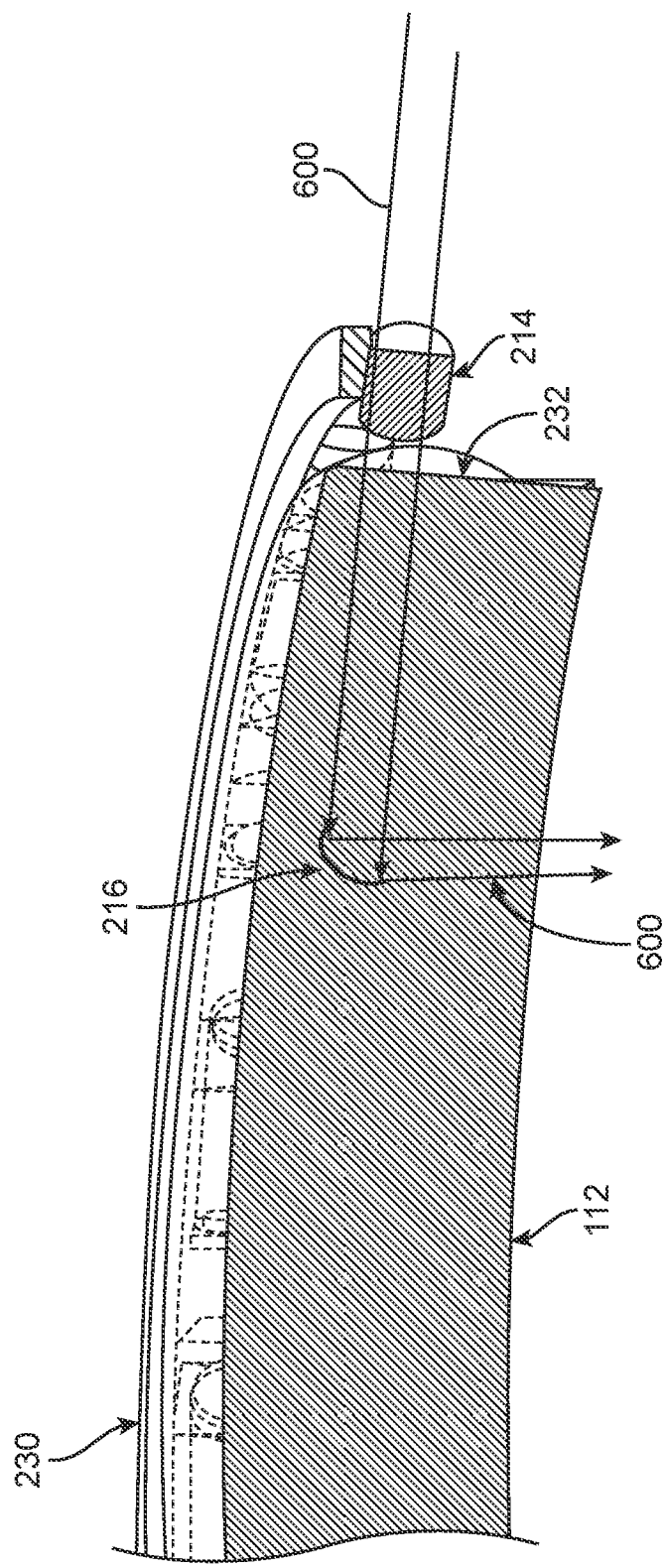
FIG. 16 shows a view of a lens in which a facet directs light from a projection module to a concave mirror, in accordance with some embodiments.
Figure 17:
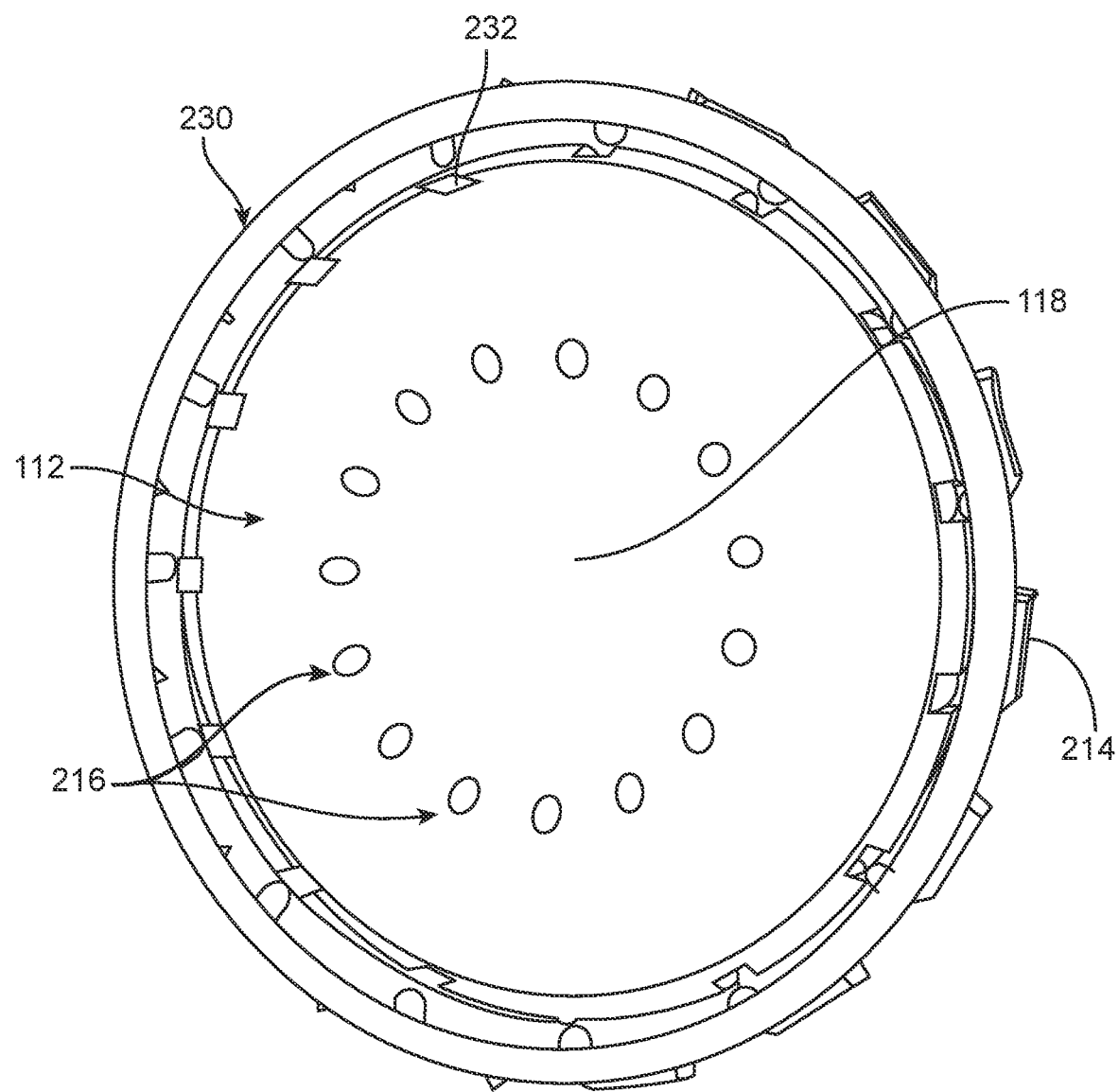
FIG. 17 shows a front view of a lens in which a facet directs light from a projection module to a concave mirror, in accordance with some embodiments.
Figure 18:
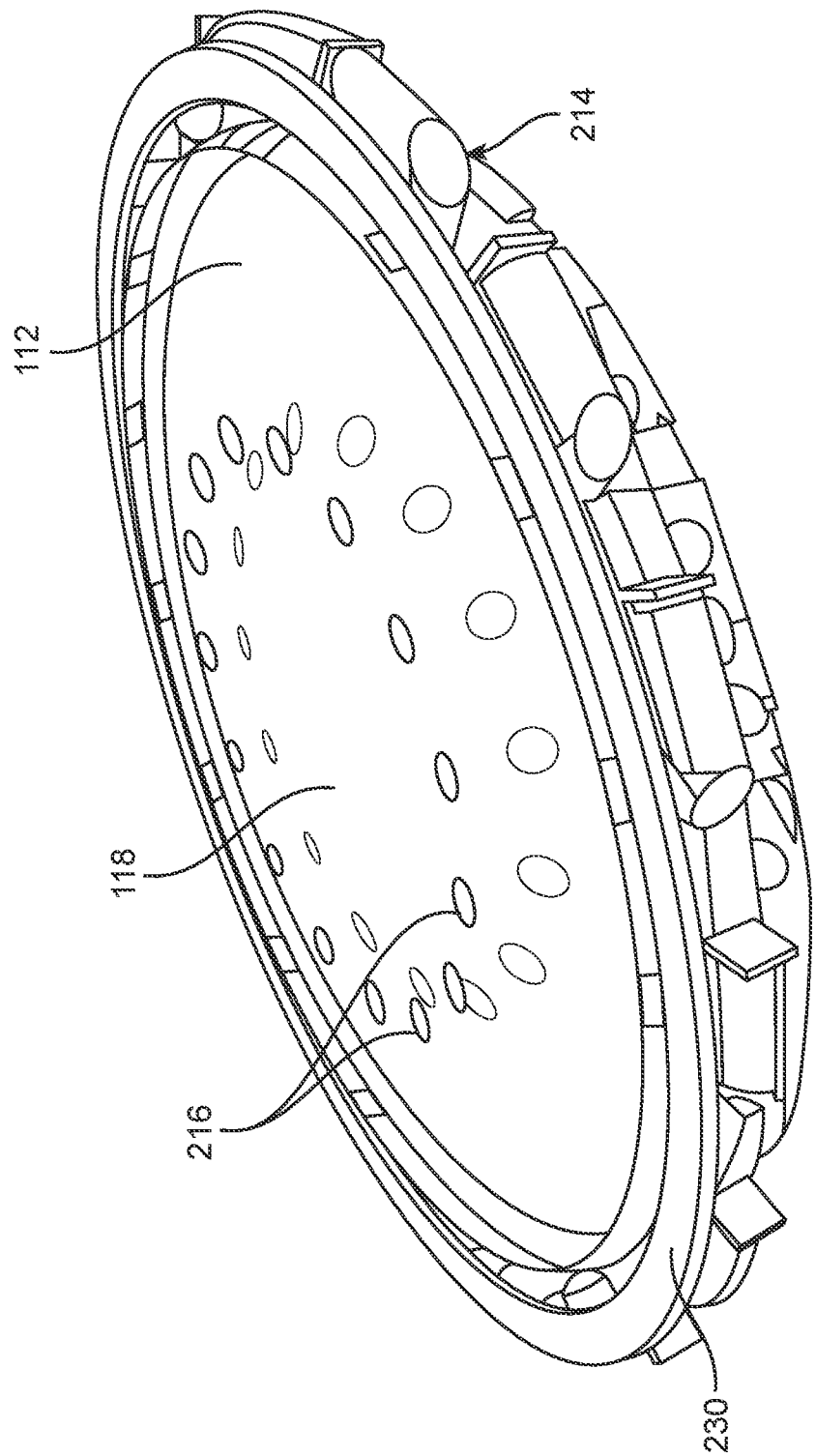
FIG. 18 shows a side view of the lens of FIG. 17, in accordance with some embodiments.
Figure 19:
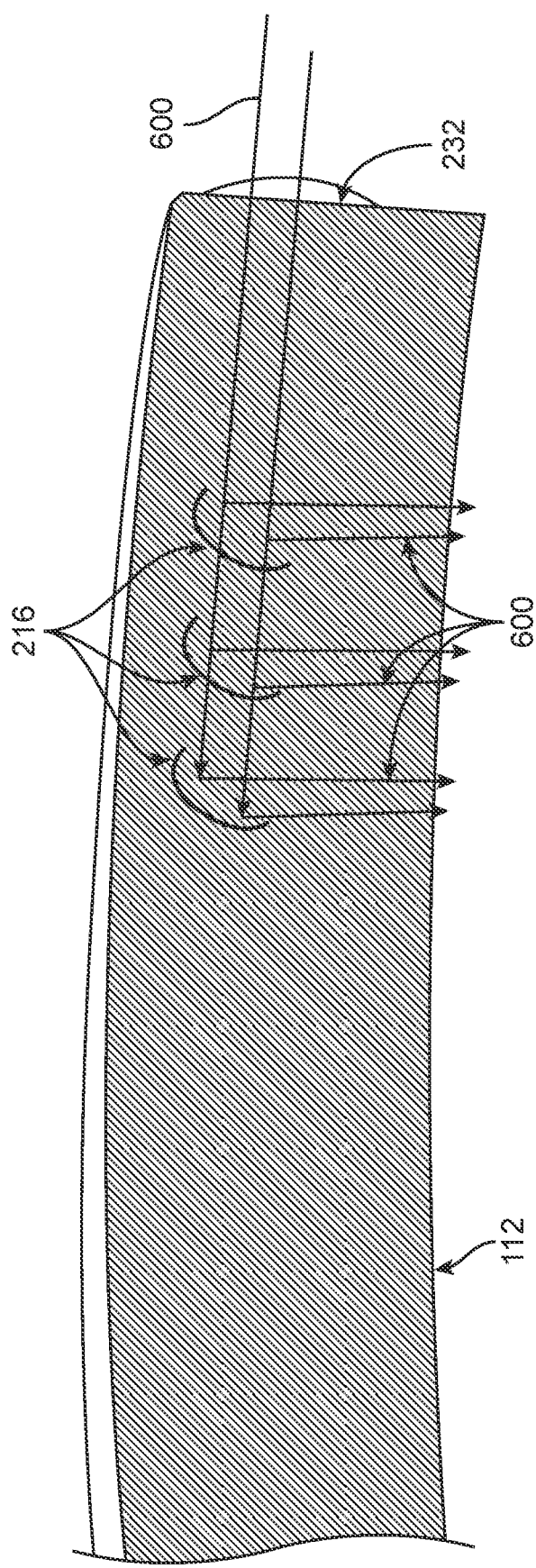
FIG. 19 shows a view of a lens in which a facet directs light from a projection module to a set of concave mirrors, in accordance with some embodiments.
Figure 20:
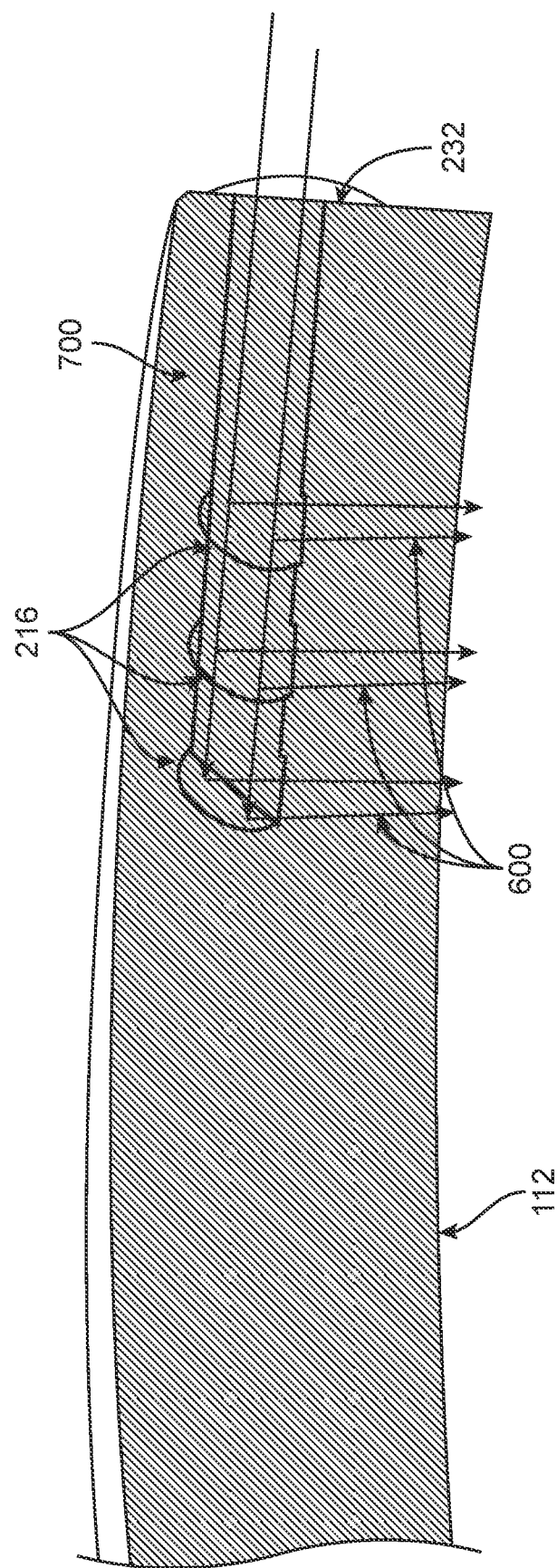
FIG. 20 shows a view of a lens in which a facet directs light from a projection module to a lightguide containing a set of concave mirrors, in accordance with some embodiments.
Figure 21:
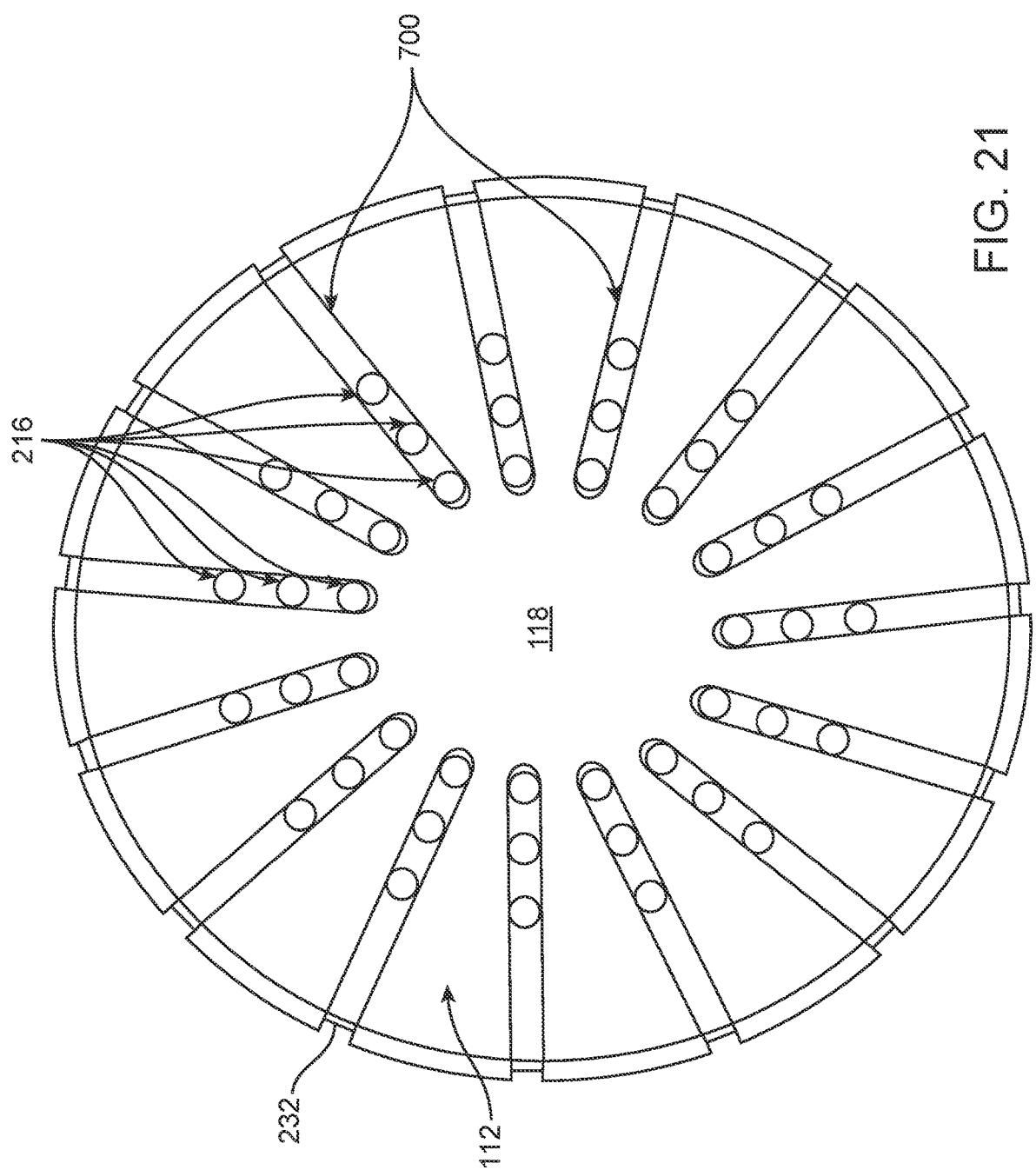
FIG. 21 shows a front view of the lens of FIG. 20, in accordance with some embodiments.

FIG. 16 shows a view of a lens 112 in which a facet 232 directs light from a projection module to a concave mirror 216, in accordance with some embodiments. FIG. 17 shows a front view of a lens 112 in which a facet 232 directs light from a projection module 214 to a concave mirror 216, in accordance with some embodiments. FIG. 18 shows a side view of the lens 112 of FIG. 17, in accordance with some embodiments. FIG. 19 shows a view of a lens 112 in which a facet 232 directs light 600 from a projection module to a concave mirror 216 among a set of concave mirrors, in accordance with some embodiments. FIG. 20 shows a view of a lens 112 in which a facet 232 directs light from a projection module to a lightguide 700 containing a set of concave mirrors 216, in accordance with some embodiments. FIG. 21 shows a front view of the lens 112 of FIG. 20, in accordance with some embodiments.

Embodiment 7

As described, the projection modules 214 and optical elements 216 may be embedded in, formed on, molded as part of, applied to, attached to, or otherwise integrated with a lens 112. Standard methods of producing spectacle lenses use lens blanks with a common spherical front surface having a specified curvature, referred to as the front base curve. The back surface of the lens is ground and polished to impart the spherical or astigmatic correction needed for a patient. In the embodiments to be described, a process can be implemented in which a rigid, semi-rigid, or flexible optical substrate 2200 (such as a film or deposition layer) is used as a base for embedding or forming the components or elements of the projection modules and/or optical elements. The back surface of the optical substrate would be designed to have a curvature that would match or could be matched (through the use of semi-rigid or flexible optical substrates) to the front base curve of a spectacle lens 112.

The electronic components may extend beyond the edge of a normally manufactured spectacle lens and would be housed within the frame of a pair of spectacles. In these embodiments, a lab would create a spectacle lens that contains the prescription needed to correct for a person's refractive error. The frames and the electro-optical assembly would be purchased by the laboratory. During the process of manufacturing the spectacles, the opto-electronics contained within the projection modules 214 and optical elements 216 would be connected as needed to microprocessors, batteries, other sensors, and any other electronics that are contained within the frames. This could be accomplished through contact electrodes or in another suitable fashion.

Embodiment 8

This embodiment is similar to that of Embodiment 7, except that instead of the back surface of the rigid, semi-rigid, or flexible optical substrate being attached to the front surface of the lens, the front surface of the rigid, semi-rigid, or flexible optical substrate is attached to the back surface of the lens. In this embodiment, the optical substrate would typically need to be sufficiently flexible to be able to be attached to the back surface of the lens.

Embodiment 9

This embodiment comprises the projection modules and optical elements described with reference to FIGS. 1B, 2, 3A, 3B, 4A, and 4B. However, in these embodiments, the projection modules and optical elements are embedded within the material of a soft or rigid gas permeable contact lens or hybrid lens. The electronic and projection components would reside in the periphery of the lens, while the mirrors and/or other optical elements could reside in the paracentral area.

Embodiment 10

Figure 22:
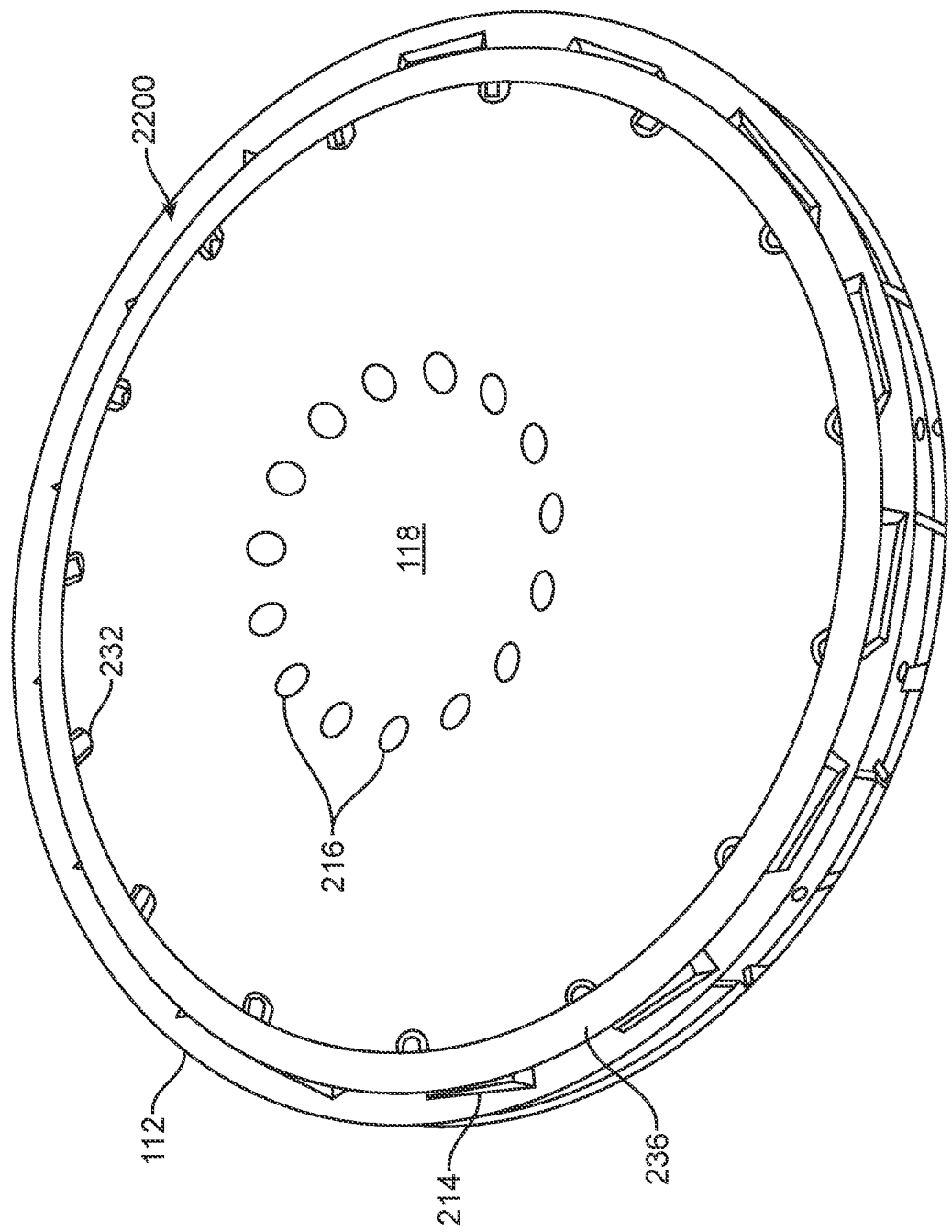
FIG. 22 shows a top view of a lens to which has been applied a film or layer incorporating the projection modules and a set of optical elements (in this case mirrors), in accordance with some embodiments.
Figure 23:
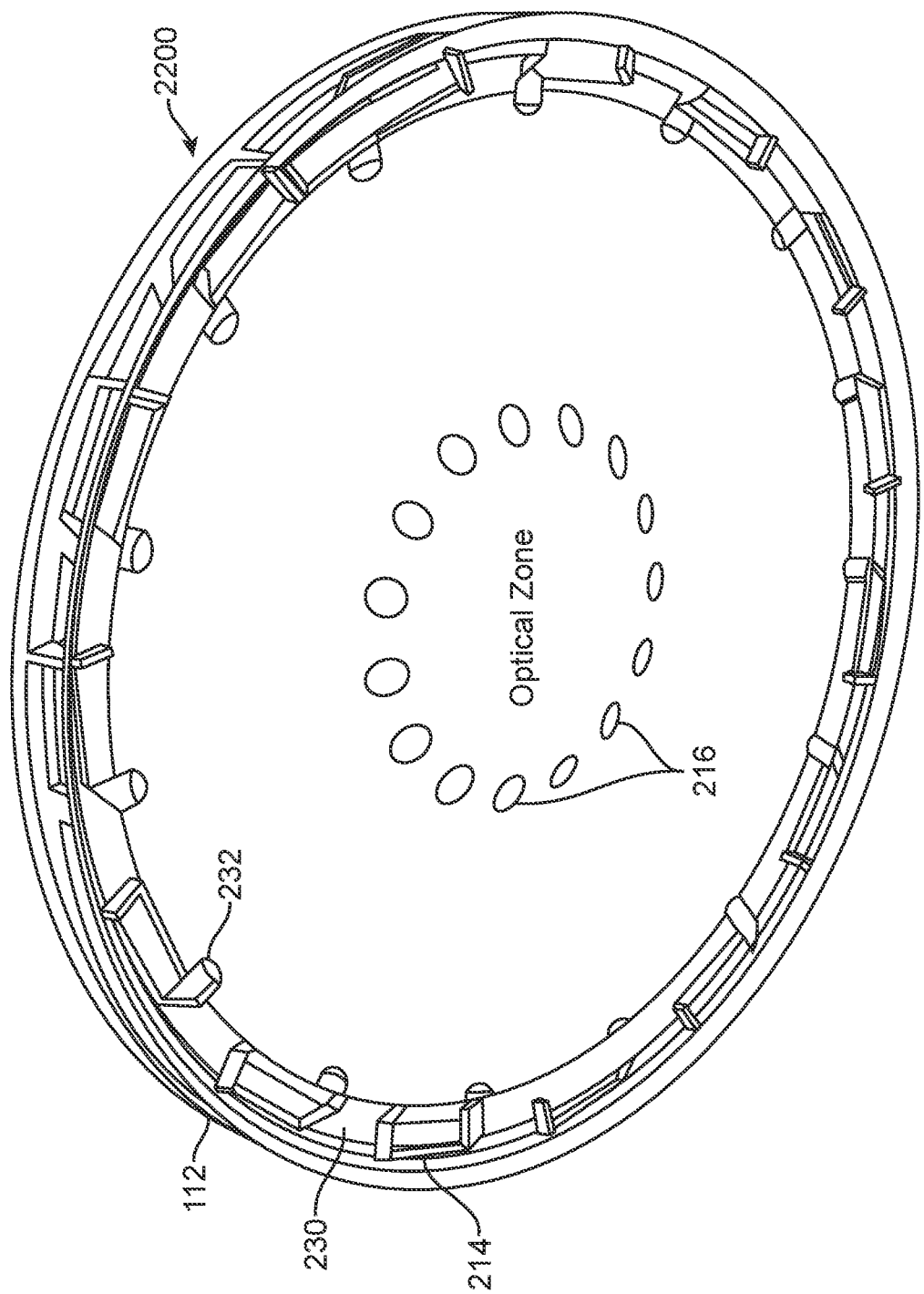
FIG. 23 shows a bottom view of the lens of FIG. 22, in accordance with some embodiments.

These embodiments comprise the projection modules and optical elements described with reference to FIGS. 1B, 2, 3A, 3B, 4A, and 4B. However, in these embodiments the projection modules and optical elements are manufactured as part of a film or layer 2200 that may be applied to an existing lens. FIG. 22 shows a top view of a lens 112 to which has been applied a film or layer 2200 incorporating the projection modules 214 and a set of optical elements 216, such as mirrors, in accordance with some embodiments. FIG. 23 shows a bottom view of the lens 112 of FIG. 22, in accordance with some embodiments.

Figure 24:
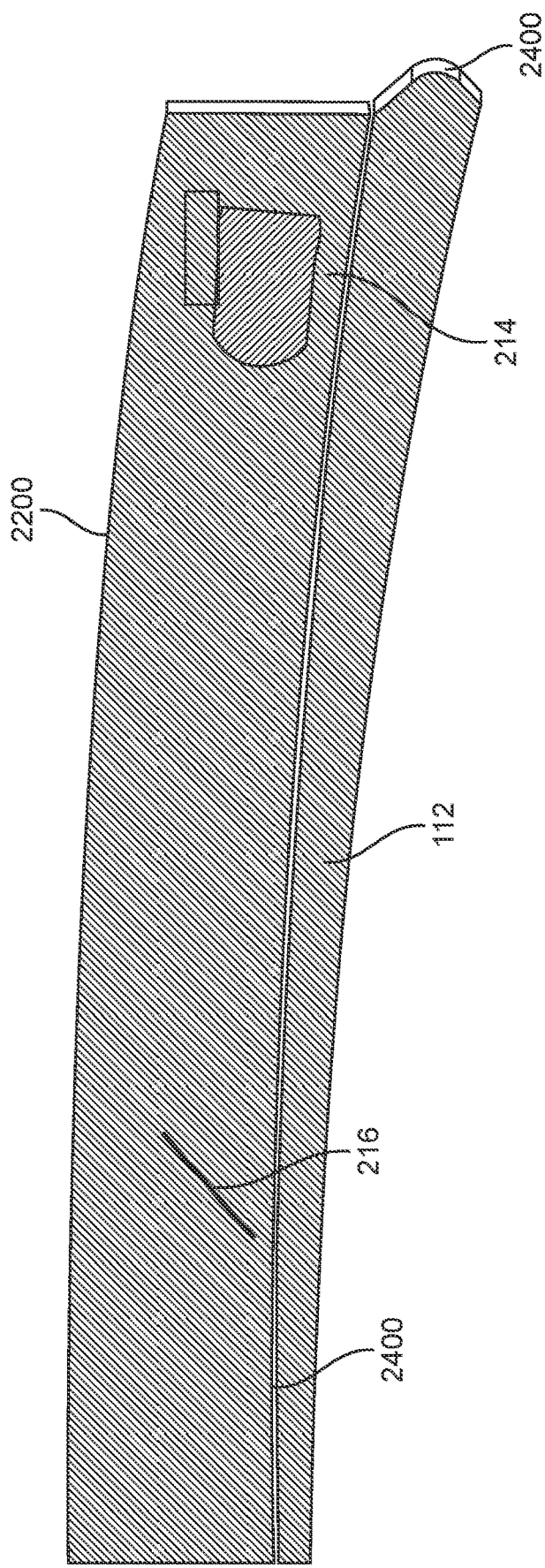
FIG. 24 shows a cross-sectional view of the applied film or layer and lens of FIG. 22, in accordance with some embodiments.
Figure 25:
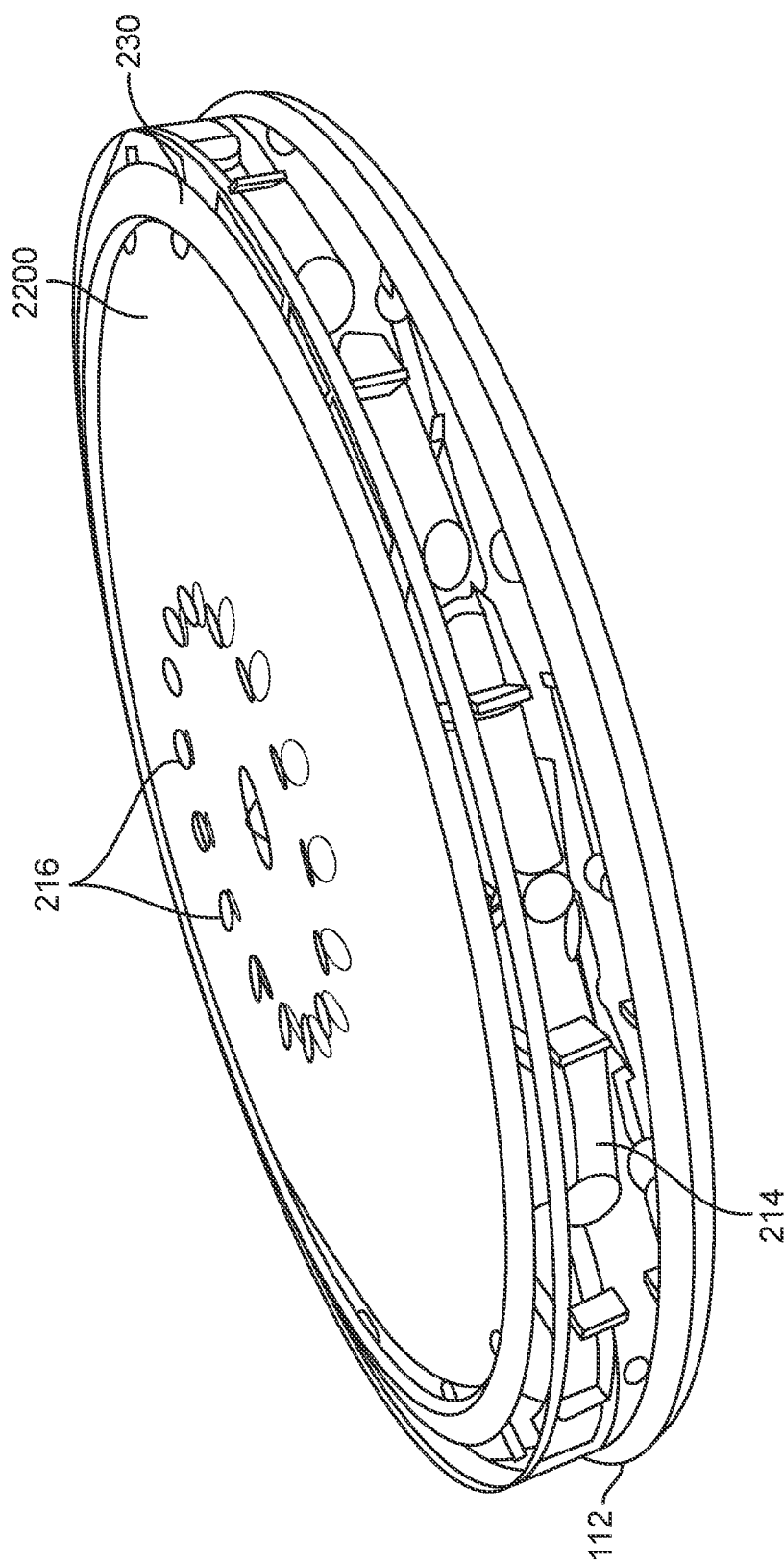
FIG. 25 shows a view of a corrective lens to the front of which has been applied a film or layer incorporating the projection modules and a set of mirrors, in accordance with some embodiments.
Figure 26:
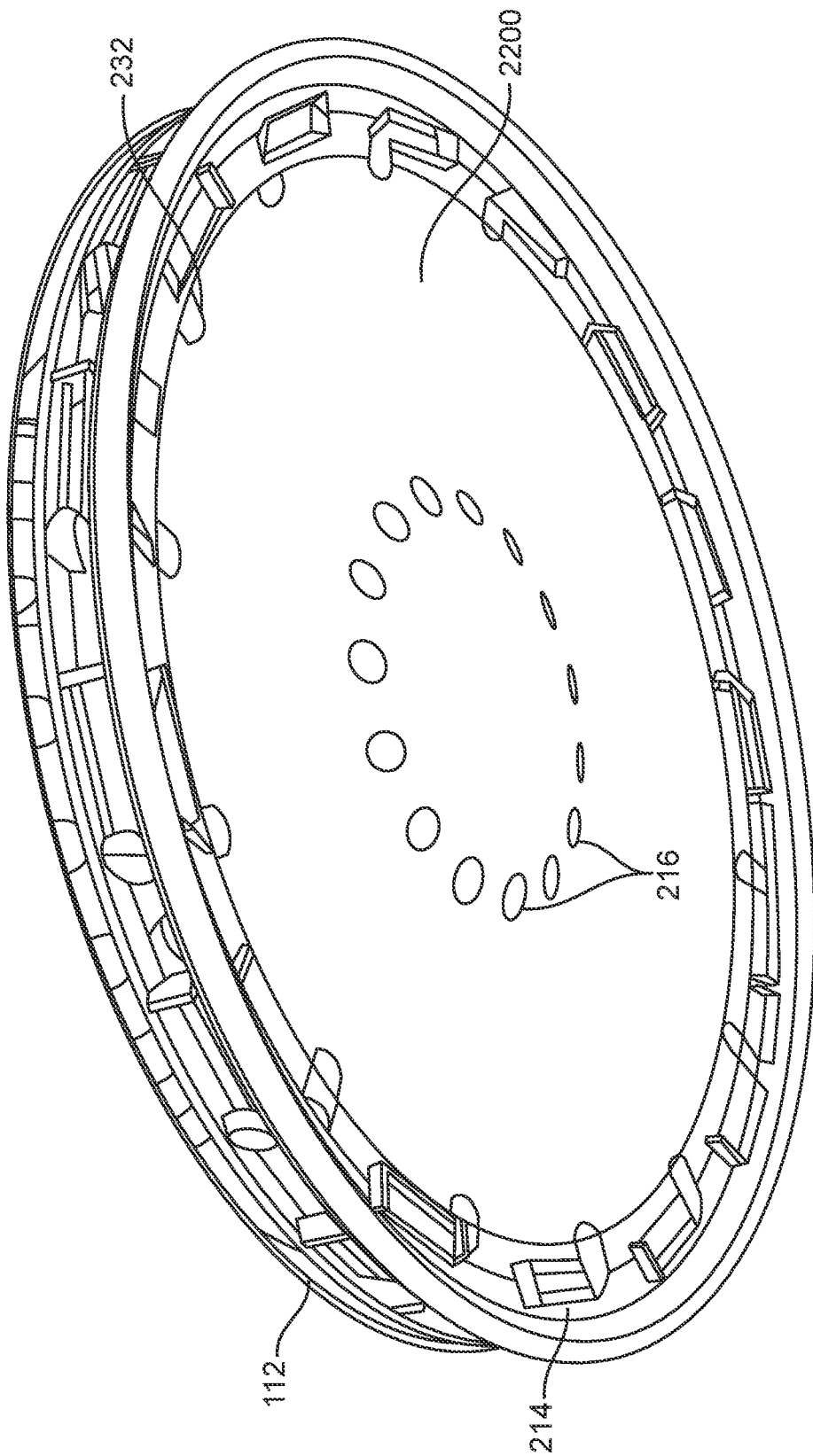
FIG. 26 shows a view of a corrective lens to the back of which has been applied a film or layer incorporating the projection modules and a set of mirrors, in accordance with some embodiments.

FIG. 24 shows a cross-sectional view of the applied film or layer 2200 and lens 112 of FIG. 22, in accordance with some embodiments. As shown in the FIG. 24, a projection module 214 and mirror 216 are embedded in or otherwise manufactured as part of a film or layer 2200 (identified as "Stick on Body" in the figure). The film or layer 2200 is applied to an existing lens 112. FIG. 25 shows a view of a corrective lens 112 to the front of which has been applied a film or layer 2200 incorporating the projection modules 214 and a set of mirrors 216, in accordance with some embodiments. The film or layer 2200 may be adhered to the lens 112 is adhesive, such as a contact adhesive, in the form of an adhesive layer 2400. The lens 112 may include a mounting bevel 2400 for mounting the lens with the attached layer 2200 to a spectacle frame. FIG. 26 shows a view of a corrective lens 112 to the back of which has been applied a film or layer 2200 incorporating the projection modules 214 and a set of mirrors 216, in accordance with some embodiments.

Although multiple embodiments of an apparatus and methods for treating refractive error in an eye have been described herein, other embodiments are possible and are included within the claims appended to this disclosure. Such other embodiments include those in which a coating or other form of shielding is applied to the sources of illumination to prevent the emission of stray light. In some embodiments, a baffle may be placed in front of a source of illumination to serve a similar purpose.

Although an example of the stimulus that may be generated is described herein, in other embodiments, the properties of the generated stimulus may be varied. These properties include the stimulus form, shape, density, and intensity of the stimulus.

The manufacture or fabrication of the elements or components of the embodiments of the apparatuses described herein may be accomplished by any suitable method or process flow. These include, but are not limited to, molding, deposition, etching, photo-lithography, pre-fabrication of the projection modules followed by inserting the pre-formed modules into facets in a lens or sections of a mold, pre-fabrication of lightguides and deposition onto a lens surface or placement into a mold or etched section, pre-fabrication of the optical elements and deposition onto a lens surface or placement into a mold or etched section, etc.

As described herein, the processor or computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor. The processor may comprise a distributed processor system, e.g. running parallel processors, or a remote processor such as a server, and combinations thereof.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the apparatuses or devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively, or in combination, the processor can be configured to combine one or more steps of one or more methods as disclosed herein. The processor as disclosed herein can be configured with instructions to perform any one or more steps of any method as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of" Finally, for ease of use, the terms "including" and "having" (and their derivatives), as used in the specification and claims, are interchangeable with and shall have the same meaning as the word "comprising."

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

The present disclosure includes the following numbered clauses:

Clause 1. An apparatus to treat refractive error of an eye, comprising: an optic; a plurality of projection modules arranged around a periphery of the optic, each of the plurality of projection modules operating to generate and direct light to form a stimulus; and a plurality of optical elements arranged on the optic to receive the light from the plurality of projection modules and direct the received light to form an image of the stimulus anterior or posterior to a peripheral region of a retina of the eye.

Clause 2. The apparatus of clause 1, wherein the optic comprises a lens.

Clause 3. The apparatus of clause 1, wherein the optic comprises a film or layer that is applied to a lens.

Clause 4. The apparatus of clause 2, wherein the lens comprises a contact lens or a lens of a pair of spectacles.

Clause 5. The apparatus of clause 1, wherein each of the plurality of projection modules further comprises: circuitry operative to activate a source of illumination in response to a control signal from a processor; a stimulus forming element arranged to form the stimulus when illuminated by the source of illumination; and a guide element to direct light from the stimulus forming element to at least one of the plurality of optical elements.

Clause 6. The apparatus of clause 5, wherein the source of illumination comprises one or more of a LED, OLED, a phosphorescent LED or a plurality of LEDs.

Clause 7. The apparatus of clause 5, wherein the source of illumination generates light in a specific wavelength band.

Clause 8. The apparatus of clause 5, wherein the source of illumination generates light in a wavelength band of no more than 25 nm.

Clause 9. The apparatus of clause 5, wherein the stimulus forming element comprises a mask, film, or reticle.

Clause 10. The apparatus of clause 1, wherein the formed image of the stimulus comprises an illuminated cross on a dark background and optionally a white cross on a black background.

Clause 11. The apparatus of clause 5, wherein the guide element comprises a lightguide.

Clause 12. The apparatus of clause 11, wherein the lightguide further comprises: a light channel configured to transmit light; a reflective element to redirect the transmitted light to form the image; and a focusing element arranged to receive the redirected light and to project the redirected light toward at least one of the plurality of optical elements.

Clause 13. The apparatus of clause 12, wherein the focusing element comprises one or more lenses.

Clause 14. The apparatus of clause 13, wherein the one or more lenses create a convergent beam of light.

Clause 15. The apparatus of clause 1, wherein each of the plurality of optical elements comprises one or more of a mirror or mirrors, a partial mirror or partial mirrors, or a lightguide.

Clause 16. The apparatus of clause 5, wherein the optic comprises a lens and each of the guide elements directs the formed stimulus to a facet of the lens, and further, wherein the facet directs the formed stimulus to at least one of the plurality of optical elements.

Clause 17. The apparatus of clause 1, wherein the optic comprises a lens of a pair of spectacles and further, wherein each of the plurality of projection modules are supported by a frame of the spectacles, and optionally embedded or partially embedded in the frame.

Clause 18. The apparatus of clause 5, wherein the optic comprises a film or layer that is applied to a lens.

Clause 19. The apparatus of clause 18, wherein each of the guide elements directs the formed stimulus to a facet of the lens, and further, wherein the facet directs the formed stimulus to at least one of the plurality of optical elements.

Clause 20. The apparatus of clause 1, wherein each of the plurality of optical elements comprises a lightguide, and further wherein each lightguide comprises a mirror or mirrors to redirect the received stimulus into the eye to form an image anterior or posterior to a peripheral region of the retina.

Clause 21. The apparatus of clause 20 wherein each lightguide comprises one or more partial mirrors, the partial mirrors operating to cause an image of the same luminance to be formed by each lightguide.

Clause 22. The apparatus of clause 5, wherein the circuitry includes a source of power, and further, wherein the processor is programmed with a set of instructions that when executed, cause the processor to generate the control signal.

Clause 23. The apparatus of clause 1, wherein the optic comprises an optical substrate having a curvature substantially the same as the front curvature of a lens of a pair of spectacles, the optic configured to fit over the lens of the pair of spectacles.

Clause 24. The apparatus of clause 1, wherein the optic comprises an optical substrate having a curvature substantially the same as the back curvature of a lens of a pair of spectacles, the optic configured to fit behind the lens of the pair of spectacles.

Clause 25. A method of manufacturing an apparatus for treating refractive error of an eye, comprising: arranging a plurality of projection modules around a periphery of an optic, each of the plurality of projection modules operating to generate and direct light to form a stimulus; and arranging a plurality of optical elements on the optic to receive the light from the plurality of projection modules and direct the received light to form an image of the stimulus anterior or posterior to a peripheral region of a retina of the eye.

Clause 26. The method of manufacturing of clause 25, wherein the optic comprises a lens.

Clause 27. The method of manufacturing of clause 25, wherein the optic comprises a film or layer that is applied to a lens.

Clause 28. The method of manufacturing of clause 26, wherein the lens comprises a contact lens or a lens of a pair of spectacles.

Clause 29. The method of manufacturing of clause 25, wherein each of the plurality of projection modules further comprises: circuitry operative to activate a source of illumination in response to a control signal from a processor; a stimulus forming element arranged to form the stimulus when illuminated by the source of illumination; and a guide element to direct light from the stimulus forming element to at least one of the plurality of optical elements.

Clause 30. The method of manufacturing of clause 29, wherein the source of illumination comprises one or more of a LED, OLED, a phosphorescent LED or a plurality of LEDs.

Clause 31. The method of manufacturing of clause 29, wherein the stimulus forming element comprises a mask or reticle.

Clause 32. The method of manufacturing of clause 25, wherein the formed image of the stimulus comprises an illuminated cross on a dark background and optionally a white cross on a black background.

Clause 33. The method of manufacturing of clause 29, wherein the guide element comprises a lightguide.

Clause 34. The method of manufacturing of clause 33, wherein the lightguide further comprises: a light channel configured to transmit light; a reflective element to redirect the transmitted light to form the image; and a focusing element arranged to receive the redirected light and to project the redirected light toward at least one of the plurality of optical elements.

Clause 35. The method of manufacturing of clause 34, wherein the focusing element comprises one or more lenses.

Clause 36. The method of manufacturing of clause 25, wherein each of the plurality of optical elements comprises one or more of a mirror or mirrors, a partial mirror or partial mirrors, or a lightguide.

Clause 37. The method of manufacturing of clause 29, wherein the optic comprises a lens and each of the guide elements directs the formed stimulus to a facet of the lens, and further, wherein the facet directs the formed stimulus to at least one of the plurality of optical elements.

Clause 38. The method of manufacturing of clause 25, wherein the optic comprises a lens of a pair of spectacles and wherein the method further comprises supporting each of the plurality of projection modules by a frame of the spectacles, and optionally embedding or partially embedding each projection module in the frame.

Clause 39. The method of manufacturing of clause 25, wherein the optic comprises a film or layer that is applied to a lens.

Clause 40. The method of manufacturing of clause 39, wherein each of the guide elements directs the formed stimulus to a facet of the lens, and further, wherein the facet directs the formed stimulus to at least one of the plurality of optical elements.

Clause 41. The method of manufacturing of clause 25, wherein each of the plurality of optical elements comprises a lightguide, and further wherein each lightguide comprises a mirror or mirrors to redirect the received stimulus into the eye to form an image anterior or posterior to a peripheral region of the retina.

Clause 42. The method of manufacturing of clause 41, wherein each lightguide comprises one or more partial mirrors, the partial mirrors operating to cause an image of the same luminance to be formed by each lightguide.

Clause 43. The method of manufacturing of clause 29, wherein the circuitry includes a source of power, and further, wherein the processor is programmed with a set of instructions that when executed, cause the processor to generate the control signal.

Clause 44. The method of manufacturing of clause 25, wherein the optic comprises an optical substrate having a curvature substantially the same as the front curvature of a lens of a pair of spectacles, the optic configured to fit over the lens of the pair of spectacles.

Clause 45. The method of manufacturing of clause 25, wherein the optic comprises an optical substrate having a curvature substantially the same as the back curvature of a lens of a pair of spectacles, the optic configured to fit behind the lens of the pair of spectacles.

Clause 46. A method of correcting refractive error of an eye, comprising: generating a stimulus by operating a plurality of projection modules arranged around a periphery of an optic, wherein each of the plurality of projection modules operates to generate and direct light to form the stimulus; and forming an image of the stimulus anterior or posterior to a peripheral region of a retina of the eye by directing light from the plurality of projection modules to a plurality of optical elements arranged on the optic, wherein the plurality of optical elements receive the light from the plurality of projection modules and direct the received light to form the image of the stimulus.

Clause 47. The method of clause 46, wherein the optic comprises a lens.

Clause 48. The method of clause 46, wherein the optic comprises a film or layer that is applied to a lens.

Clause 49. The method of clause 47, wherein the lens comprises a contact lens or a lens of a pair of spectacles.

Clause 50. The method of clause 46, wherein each of the plurality of projection modules further comprises: circuitry operative to activate a source of illumination in response to a control signal from a processor; a stimulus forming element arranged to form the stimulus when illuminated by the source of illumination; and a guide element to direct light from the stimulus forming element to at least one of the plurality of optical elements.

Clause 51. The method of clause 50, wherein the source of illumination comprises one or more of a LED, OLED, a phosphorescent LED or a plurality of LEDs.

Clause 52. The method of clause 50, wherein the stimulus forming element comprises a mask or reticle.

Clause 53. The method of clause 46, wherein the formed image of the stimulus comprises an illuminated cross on a dark background and optionally a white cross on a black background.

Clause 54. The method of clause 50, wherein the guide element comprises a lightguide.

Clause 55. The method of clause 54, wherein the lightguide further comprises: a light channel configured to transmit light; a reflective element to redirect the transmitted light to form the image; and a focusing element arranged to receive the redirected light and to project the redirected light toward at least one of the plurality of optical elements.

Clause 56. The method of clause 55, wherein the focusing element comprises one or more lenses.

Clause 57. The method of clause 46, wherein each of the plurality of optical elements comprises one or more of a mirror or mirrors, a partial mirror or partial mirrors, or a lightguide.

Clause 58. The method of clause 50, wherein the optic comprises a lens and each of the guide elements directs the formed stimulus to a facet of the lens, and further, wherein the facet directs the formed stimulus to at least one of the plurality of optical elements.

Clause 59. The method of clause 46, wherein the optic comprises a lens of a pair of spectacles and wherein the method further comprises supporting each of the plurality of projection modules by a frame of the spectacles, and optionally embedding or partially embedding each projection module in the frame.

Clause 60. The method of clause 46, wherein the optic comprises a film or layer that is applied to a lens.

Clause 61. The method of clause 60, wherein each of the guide elements directs the formed stimulus to a facet of the lens, and further, wherein the facet directs the formed stimulus to at least one of the plurality of optical elements.

Clause 62. The method of clause 61, wherein each of the plurality of optical elements comprises a lightguide, and further wherein each lightguide comprises a mirror or mirrors to redirect the received stimulus into the eye to form an image anterior or posterior to a peripheral region of the retina.

Clause 63. The method of clause 62, wherein each lightguide comprises one or more partial mirrors, the partial mirrors operating to cause an image of the same luminance to be formed by each lightguide.

Clause 64. The method of clause 50, wherein the circuitry includes a source of power, and further, wherein the processor is programmed with a set of instructions that when executed, cause the processor to generate the control signal.

Clause 65. The method of clause 46, wherein the optic comprises an optical substrate having a curvature substantially the same as the front curvature of a lens of a pair of spectacles, the optic configured to fit over the lens of the pair of spectacles.

Clause 66. The method of clause 46, wherein the optic comprises an optical substrate having a curvature substantially the same as the back curvature of a lens of a pair of spectacles, the optic configured to fit behind the lens of the pair of spectacles.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A method of correcting refractive error of an eye, comprising:
generating a stimulus by operating a plurality of projection modules arranged around a periphery of an optic, wherein each of the plurality of projection modules operates to generate and direct light to form the stimulus; and
forming an image of the stimulus anterior or posterior to a peripheral region of a retina of the eye by directing light from the plurality of projection modules to a plurality of optical elements arranged on the optic, wherein the plurality of optical elements receives the light from the plurality of projection modules and directs the received light to form the image of the stimulus, wherein each of the plurality of projection modules further comprises: circuitry operative to activate a source of illumination in response to a control signal from a processor; a stimulus forming element arranged to form the stimulus when illuminated by the source of illumination; and a guide element to direct light from the stimulus forming element to at least one of the plurality of optical elements.

2. The method of claim 1, wherein the optic comprises a lens.

3. The method of claim 1, wherein the optic comprises a film or layer that is applied to a lens.

4. The method of claim 2, wherein the lens comprises a contact lens or a lens of a pair of spectacles.

5. The method of claim 1, wherein the source of illumination comprises one or more of a LED, OLED, a phosphorescent LED or a plurality of LEDs.

6. The method of claim 1, wherein the stimulus forming element comprises a mask or reticle.

7. The method of claim 1, wherein the formed image of the stimulus comprises an illuminated cross on a dark background.

8. The method of claim 1, wherein the guide element comprises a lightguide.

9. The method of claim 8, wherein the lightguide comprises: a light channel configured to transmit light; a reflective element to redirect the transmitted light to form the image; and a focusing element arranged to receive the redirected light and to project the redirected light toward at least one of the plurality of optical elements.

10. The method of claim 9, wherein the focusing element comprises one or more lenses.

11. The method of claim 1, wherein each of the plurality of optical elements comprises one or more of a mirror or mirrors, a partial mirror or partial mirrors, or a lightguide.

12. The method of claim 1, wherein the optic comprises a lens and each of the guide elements directs the light to a facet of the lens, and further, wherein the facet directs the light to at least one of the plurality of optical elements.

13. The method of claim 1, wherein the optic comprises a lens of a pair of spectacles and wherein the method further comprises supporting each of the plurality of projection modules by a frame of the spectacles.

14. The method of claim 1, wherein the optic comprises a film or layer that is applied to a lens.

15. The method of claim 1, wherein each of the guide elements directs the light to a facet of the lens, and further, wherein the facet directs the light to at least one of the plurality of optical elements.

16. The method of claim 15, wherein each of the plurality of optical elements comprises a lightguide and wherein each lightguide comprises a mirror or mirrors to redirect the received light into the eye to form the image anterior or posterior to the peripheral region of the retina.

17. The method of claim 16, wherein each lightguide comprises one or more partial mirrors, the one or more partial mirrors operating to cause an image of a same luminance to be formed by each lightguide.

18. The method of claim 1, wherein the circuitry includes a source of power and wherein the processor is programmed with a set of instructions that when executed, cause the processor to generate the control signal.

19. The method of claim 1, wherein the optic comprises an optical substrate having a curvature substantially conforming to a back curvature of a lens of a pair of spectacles, the optic configured to fit behind the lens of the pair of spectacles.

* * * * *